US009511054B2

(12) United States Patent
Arnou

(10) Patent No.: US 9,511,054 B2
(45) Date of Patent: *Dec. 6, 2016

(54) HISTAMINE BALANCE RESTORATION METHODS

(71) Applicant: BioHealthonomics Inc., Santa Monica, CA (US)

(72) Inventor: Cristian Arnou, Santa Monica, CA (US)

(73) Assignee: BioHealthonomics Inc., Santa Monica, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/684,174

(22) Filed: Apr. 10, 2015

(65) Prior Publication Data
US 2015/0209331 A1  Jul. 30, 2015

Related U.S. Application Data

(63) Continuation of application No. 14/315,206, filed on Jun. 25, 2014, now Pat. No. 9,023,881, which is a continuation-in-part of application No. PCT/US2013/046420, filed on Jun. 18, 2013.

(60) Provisional application No. 61/733,630, filed on Dec. 5, 2012, provisional application No. 61/867,966, filed on Aug. 20, 2013, provisional application No. 62/002,613, filed on May 23, 2014.

(51) Int. Cl.
*A61K 31/415* (2006.01)
*A61K 31/417* (2006.01)
*A61K 45/06* (2006.01)

(52) U.S. Cl.
CPC ............. *A61K 31/417* (2013.01); *A61K 45/06* (2013.01)

(58) Field of Classification Search
USPC ........................................................ 514/400
See application file for complete search history.

(56) References Cited

U.S. PATENT DOCUMENTS

| | | | |
|---|---|---|---|
| 4,544,629 A | 10/1985 | Rice et al. | |
| 5,961,969 A | 10/1999 | Hellstrand et al. | |
| 6,071,942 A | 6/2000 | Hellstrand et al. | |
| 6,221,893 B1 | 4/2001 | Hellstrand et al. | |
| 6,613,788 B1 | 9/2003 | Hellstrand et al. | |
| 9,023,881 B2 * | 5/2015 | Arnou | A61K 45/06 514/400 |
| 2002/0010194 A1 | 1/2002 | Levin | |
| 2003/0143195 A1 * | 7/2003 | Pinsker | A61K 9/006 424/85.2 |
| 2006/0002913 A1 | 1/2006 | Gehlson | |

FOREIGN PATENT DOCUMENTS

WO    WO 99/25341    5/1999

OTHER PUBLICATIONS

Bartleson, Treatment of Migraine Headaches, Mayo Clin. Proc. 1999; 74; 702-708).
Cacabelos, et al., Brain Histamine in Alzheimer's Disease, Methods Find Exp Clin Pharmacol. May 1989;11(5):353-60.
Haas, et al., Histamine in the Nervous System, Physiol. Rev., 2008, vol. 88:1183-1241.
King WP., The use of low-dose histamine therapy in otolaryngology, Ear Nose Throat J. May 1999;78(5):366-70.
Krabbe, et al., Headache provocation by continuous intravenous infusion of histamine. Clinical results and receptor mechanisms, Pain. Apr. 1980;8(2):253-9.
Lassen, et al., Histamine induces migraine via the H1-receptor. Support for the NO hypothesis of migraine, Neuroreport. Jul. 31, 1995;6(11):1475-9.
Maintz et al., Histamine and histamine intolerance, Am. J. Clin. Nutr., 2007, vol. 85:1185-1196.
Millan-Guerrero, et al., Histamine as a therapeutic alternative in migraine prophylaxis: a randomized, placebo-controlled, double-blind study. Headache. 1999 vol. 39(8): 576-580.
Millan-Guerrero, et al., Subcutaneous histamine versus sodium valproate randomized, controlled, double-blind study, Eur. J. of Neurol., 2007, vol. 14:1079-1084.
Millan-Guerrero, et al., Subcutaneous histamine versus botulinum toxin type A in migraine prophylaxis: a randomized, double-blind study, Eur. J. of Neurol., 2009, vol. 16:88-94.
Millan-Guerrero Ro, et al., Subcutaneous Histamine versus Topiramate in Migraine Prophylaxis: A Double-Blind Study, Eur Neurol; vol. 59:237-242 (2008).
Millan-Guerrero Ro, et al., Nα-Methyl Histamine Safety and Efficacy in Migraine Prophylaxis: Phase III Study Can. J. Neurol. Sci., vol. 33: 195-199 (2006).
Millan-Guerrero Ro, et al., Nα-Methylhistamine Safety and Efficacy in Migraine Prophylaxis: Phase I and Phase II Studies, Headache vol. 43:389-394 (2003).
Millán-Guerreroa Ro, et al., Nueva alternativa terapéutica en profilaxis de migraña con histamina como agonista de receptores H3 Gac Méd Méx vol. 144 No. 4: 291-295 (2008).
Perz et al., Histamine dihydrochloride for the treatment of acute myeloid leukemia, malignant melanoms and renal cell carcinoma, Future Oncology, vol. 4(2):169-177 (2008).
Pietrini, et al., Prophylactic activity of increasing doses of intravenous histamine in refractory migraine: Retrospective observations of a series of patients with migraine without aura, Current Therapeutic Research, Jan.-Feb. 2004, vol. 65(1): 70-78.
Rinne, et al., Increased brain histamine levels in Parkinson's disease but not in multiple system atrophy, J. of Neurochem., 2002, vol. 81:954-960.

(Continued)

*Primary Examiner* — Rei-Tsang Shiao
(74) *Attorney, Agent, or Firm* — Knobbe Martens Olson & Bear LLP

(57) ABSTRACT

Several embodiments provided herein relate to histamine dosing regimens are and uses of such regimens in the restoration of histamine balance in subjects suffering from, for example, histapenia and/or histadelia. Several embodiments also relate to the use of histamine dosing regimens for the treatment and/or prevention of migraine headaches.

18 Claims, 7 Drawing Sheets

(56) References Cited

OTHER PUBLICATIONS

Sander, et al., Selective expression of histamine receptor H1R, H2R, and H4R, but not H3R, in the human intestinal tract, Gut, 2006, vol. 55:498-504.
Suzuki, et al., Histamine contents of blood plasma and cells in patients with myeolgenous leukemia, Cancer, 1971, vol. 28: 384-388.
Zdravkovic, et al., Histamine Blood Concentrations in Ischemic Heart Disease Patients, J. of Biomedicine and Biotechnology, 2011, vol. 2011:1-8.
PCT/US2013/046420, Jun. 18, 2013, Methods for Restoration of Histamine Balance.
U.S. Appl. No. 14/315,206, filed Jun. 25, 2014, Methods for Restoration of Histamine Balance.

* cited by examiner

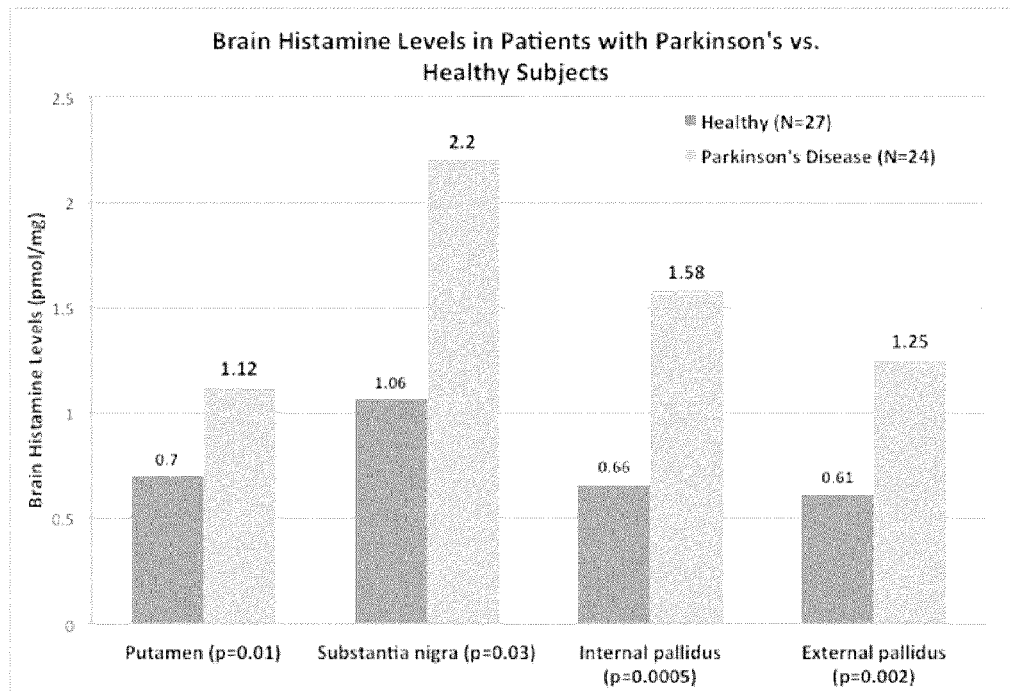
Figure 6: Brain Histamine Levels in Patients with Parkinson's vs. Healthy Subjects
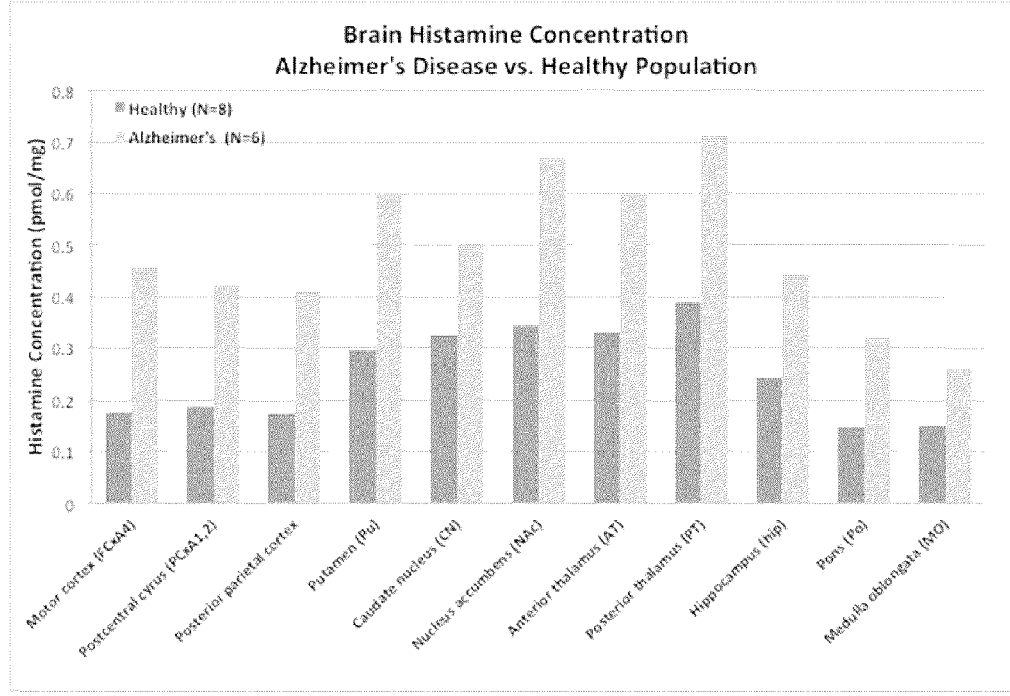
Figure 7: Brain Histamine Concentration in Patients with Alzheimer's Disease vs. Healthy Population

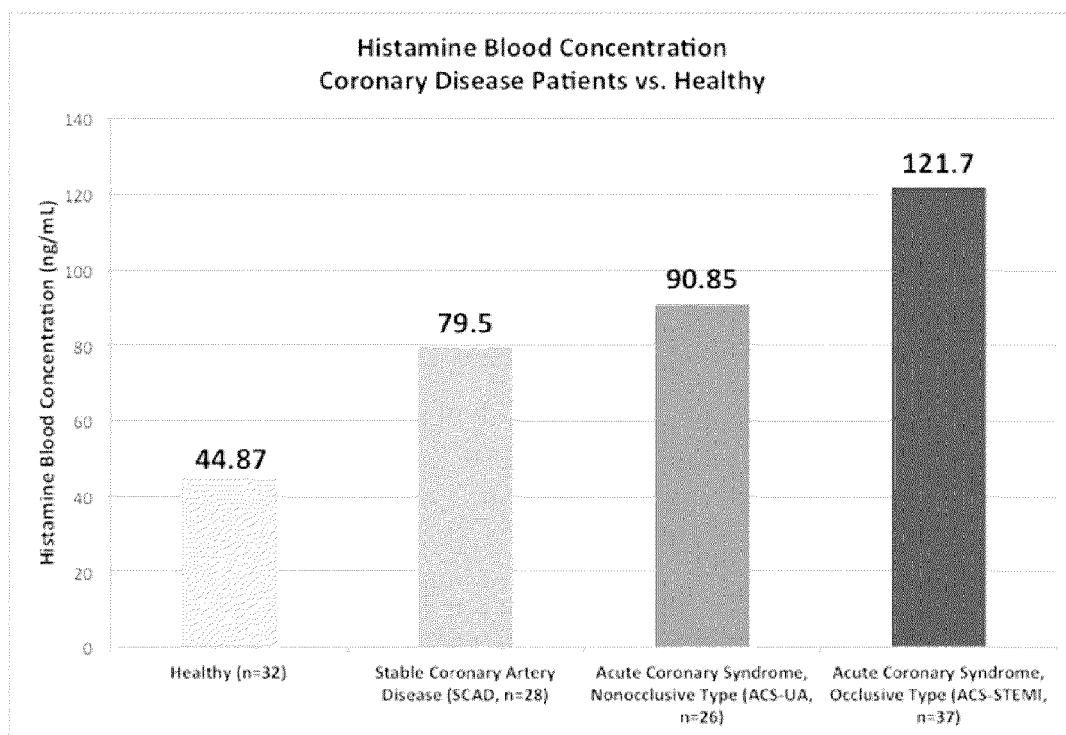
Figure 8: Histamine Blood Concentration in Patients with Coronary Disease vs. Healthy Population
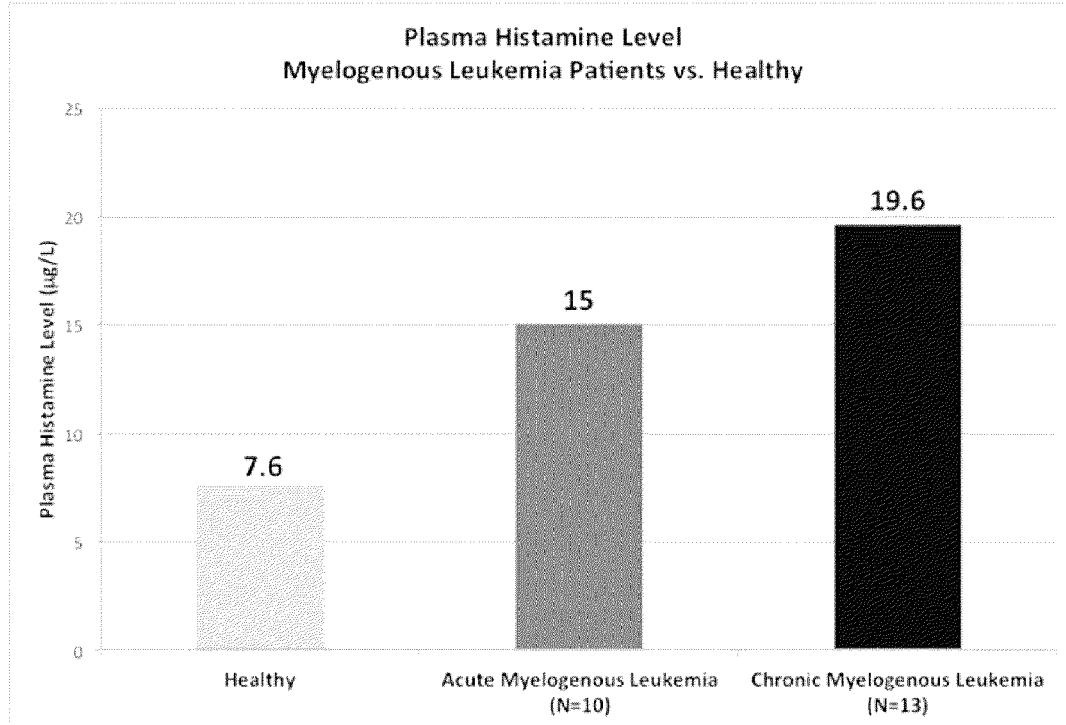
Figure 9: Plasma Histamine Levels in Patients with Myelogenous Leukemia vs. Healthy Population

HISTAMINE BALANCE RESTORATION METHODS

RELATED CASES

This application is a continuation of U.S. patent application Ser. No. 14/315,206, filed Jun. 25, 2014, which is a continuation in part of International Application No. PCT/US2013/046420, filed Jun. 18, 2013, which claims the benefit of U.S. Provisional Application No. 61/733,630, filed Dec. 5, 2012. This application also claims the benefit of U.S. Provisional Application No. 61/867,966, filed on Aug. 20, 2013 and U.S. Provisional Application No. 62/002,613, filed on May 23, 2014. The entire disclosure of each of the applications listed above is incorporated by reference herein.

BACKGROUND

Field

Several embodiments of the present invention relate generally to methods for the restoration of histamine balance. In particular, several embodiments related restoring histamine levels to normal ranges in order to treat various illnesses or disorders.

Description of the Related Art

Histamine, also referred to chemically as 2-(1H-imidazol-4-yl)ethanamine is composed of an imidazole ring and an amino group connected by a chain of two carbon atoms (see FIG. 1). Histamine is the decarboxylation product of the amino acid histidine and is associated with local immune responses to foreign pathogens. For example, the granules of mast cells or white blood cells generate and/or store histamine which is released upon injury or exposure to allergens. Histamine also functions as a neurotransmitter and plays a role in the pathways of gastric acid secretion in the stomach.

SUMMARY

Dysregulation or imbalances of the histamine system can be a leading contributor to a variety of disease states and symptoms, many of which can be debilitating or life-disruptive. For example, abnormally high histamine levels can lead to excessive allergies (or hyperactive responses to allergens), hyperactivity, compulsive or obsessive behavior, vertigo, inner ear pressure, depression, anxiety, panic attacks, migraine headaches, heightened emotional sensitivity and/or suicidal tendencies. Reduced histamine levels can lead to depressed metabolism and/or weight gain, paranoia, grandiosity, hallucinations (e.g., classic schizophrenic symptoms), tinnitus, hirsutism, visual and auditory abnormalities, anxiety and food sensitivities. The potential costs (both emotional and financial) of histamine imbalance, be they to an individual person or family, related to societal lost productivity and/or burdens on the medical system, are immense. In 2012 America will have spent $200 billion in direct costs for those with Alzheimer's Disease. Caring for people with Alzheimer's Disease is estimated to cost at least $20 trillion over the next 40 years. Furthermore, the economic burden of Parkinson's disease is at least $14.4 billion a year with an estimate that the prevalence of Parkinson's disease will more than double by year 2040.

Several embodiments of the present invention relate to the use of agents that up-regulate or down-regulate expression and/or activity of one or more histamine receptors. Histamine agonists and antagonists, naturally-occurring or synthetic, are provided in several embodiments. For example, in one embodiment, titrated histamine dosing regimens are used to restore normal histamine function. The dosing regimens are useful, in several embodiments, for restoring histamine function in patients having deficient or excessive levels of histamine, and can be used to treat or prevent any disorders in which histamine imbalance plays a causative role.

Although histamine is used as the therapeutic agent in many embodiments, the invention is not limited to the administration of histamine. For example, therapeutic agents that mimic the effects of histamine are used in some embodiments. Histamine agonists, antagonists, and other agents that interact or interfere with histamine receptors are used as therapeutic agents in several embodiments. Therapeutic agents may, for example, provide stop the progression of symptoms, or may reduce or prevent the onset or severity of symptoms. A surprising versatile dosing regimen has been developed for the administration of histamine, or other therapeutic agent, that relies, in several embodiments, on sequential dosing segments. In several embodiments, each segment includes a plurality of escalating doses. For example, in one embodiment, the regimen comprises a plurality of dosing segments, each comprising a plurality of doses, wherein each segment is defined by the same volume for every dose and the same time interval between every dose, but concentrations of the therapeutic agent (e.g., histamine) are increased from dose to dose, and each successive segment is defined by a greater dosing volume than the previous segment and a longer time interval between doses. The administration of histamine or other therapeutic agent, as used herein, includes the administration of its pharmaceutically acceptable salt (such as, for example, histamine phosphate, histamine dihydrochloride or any other histamine salt). Thus, references to the administration of histamine encompass the administration of pharmacologically acceptable salts and forms in several embodiments. A histamine receptor activator includes but is not limited to histamine (and its pharmacologically acceptable salts and other forms). Moreover, in several embodiments, adjunct therapeutic interventions are used, either in place of, or in conjunction with administration of histamine and/or an additional therapeutic agent. For example, in several embodiments, an electromagnetic device is used to generate a magnetic field that can be focused (or applied diffusely) to a subject having imbalanced histamine levels. In several embodiments, electromagnetic energy is delivered to a subject to return histamine levels to within normal ranges. In some embodiments, the electromagnetic energy is tailored (e.g., by frequency, wavelength, field strength, etc.) to target one or more specific histamine receptors. In several embodiments, the use of electromagnetic devices acts synergistically with administration of histamine to return histamine levels to normal ranges. However, as discussed above, in several embodiments, such devices are used independent of histamine administration (or administration of other therapeutic agents).

Thus, in several embodiments, the invention comprises or consists essentially of an escalating dosing regimen comprising in sequential order (a) a first dosing segment comprising two or more sequential doses of a therapeutic agent (e.g., histamine) separated by one or more equal time intervals (the "first time interval"), wherein the doses increase in histamine concentration from dose to dose while the administered volume of each dose stays constant; and (b) a second dosing segment comprising two or more sequential doses of a therapeutic agent (e.g., histamine) separated by one or more equal time intervals (the "second time interval"), wherein the doses increase in concentration from dose to dose while the administered volume of each dose stays constant; wherein the volume of each dose in the second dosing segment is greater than the volume of each dose in the first dosing segment, and the second time interval is longer than the first time interval. In several embodiments, the invention comprises a multi-variable approach for increasing or decreasing histamine levels. The multi-variable approach is beneficial in several embodiments because physiological parameters can be more finely-tuned. For example, cellular distribution and receptor contact can be modulated to achieve selective activation of certain histamine receptors, while leaving other histamine receptors substantially unaffected.

In several embodiments, the invention includes administering (or instructing the administration of) several doses of a therapeutic agent (such as histamine or a histamine salt), as described herein in various embodiments. For example, in some embodiments, the invention includes administering a first therapy segment that comprises or consists essentially of (i) activating a histamine H3 receptor by administering to a subject a first dose of a therapeutic agent (such as histamine or a histamine salt); (ii) activating a histamine H4 receptor by administering a second dose of the therapeutic agent; (iii) activating a histamine H1 receptor by administering a third dose of the therapeutic agent; and (iv) activating a histamine H2 receptor by administering a fourth dose of the therapeutic agent. In additional embodiments, the invention includes administering a first therapy segment that comprises or consists essentially of (i) activating a histamine receptor selected from the group consisting of at least one of a histamine H3 receptor and a histamine H4 receptor by administering to a subject a first dose of a therapeutic agent (such as histamine or a histamine salt) in the range of 0.01 pg to 10 pg; (ii) activating a histamine receptor selected from the group consisting of at least one of a histamine H3 receptor and a histamine H4 receptor by administering a second dose of the therapeutic agent; (iii) activating a histamine H1 receptor by administering a third dose of the therapeutic agent; and (iv) activating a histamine H2 receptor by administering a fourth dose of the therapeutic agent. A second therapy segment having individual doses is further administered in which the total amount of therapeutic agent is greater than the total amount given in the first therapy segment. A third therapy segment having individual doses is further administered in which the total amount of the therapeutic agent is greater than the amount given in the second therapy segment. A fourth, fifth, sixth, etc. therapy segment with escalating total dose amounts may be optionally administered. In one embodiment, the invention includes of a kit or regimen that comprises or consists essentially of a therapeutic agent (such as histamine or a histamine salt) provided in total amount (which can be provided in single one-time disposable vials, syringes, or ampules) ranging from about 200 ng to 600 ng for the first therapy segment, 2 times as much in the second therapy segment, and 1.5 times as much (as compared to the second therapy segment) in the third therapy segment. As an example, if the total amount of a therapy segment is 1000 ng, four vials of individual doses of 1 ng, 10 ng, 100 ng, and 889 ng can be provided. The volumes of the doses are also altered in several embodiments. The varying volumes are particularly beneficial, in some embodiments, because increased volumes provide for a different distribution and/or pharmacokinetic profile. In some embodiments, the ratio of total amounts given in each therapy segment is 1:2:3 (for three segments), 1:2:3:4 (for four segments), 1:2:3:4:5 (for five segments). In some embodiments, the ratio of individual doses within in a given therapy segment is $1:10^3:10^6:3.5 \times 10^6$.

In some embodiments, the method is used to treat imbalances of histamine (the imbalance being evidenced by sub-optimal or supra-optimal histamine levels in the bloodstream and/or urine, and/or other symptoms or characteristics of histamine imbalance). Thus, in several embodiments, there is provided a method of lowering histamine levels in a subject (e.g., a human patient) having a histamine level above a level required for optimum histamine function (as in histadelia), comprising administering histamine thereof to the subject according to the dosing regimens disclosed herein.

As used herein, the terms "treating" and "treatment", shall be given their ordinary meanings and shall also include providing a therapy to a patient with the intent to cure, ameliorate, stabilize, or prevent a disease, pathological condition, or disorder. The terms include active treatment (e.g., treatment directed specifically toward the improvement of a disease, pathological condition, or disorder) and causal treatment (e.g., treatment directed toward removal of the cause of the associated disease, pathological condition, or disorder). In addition, these terms shall also include palliative treatment (e.g., treatment designed for the relief of symptoms), preventative treatment (e.g., treatment directed to minimizing or partially or completely inhibiting the development of an associated disease, pathological condition, or disorder) and supportive treatment (e.g., treatment employed to supplement another specific therapy directed toward the improvement of the associated disease, pathological condition, or disorder).

In several embodiments, the invention comprises selective activation and deactivation of the histamine receptors, namely H1, H2, H3 and H4. Histamine or other therapeutic agents that bind or block these receptors, or increase or decrease the ability of histamine (endogenous or exogenous histamine) to bind to the receptors are used in several embodiments. In some embodiments, the invention comprises the downregulation of the H1 receptor and the upregulation of one, two or all of the H2, H3 and H4 receptor. In several embodiments, the invention includes therapeutic agents that regulate the endogenous histamine system. These therapeutic agents are provided in dosing schedules as described herein according to several embodiments. Thus, instead of (or in addition to) affecting histamine receptors directly, a therapeutic agent that increases or decreases the manufacture, release, modification, uptake or degradation of histamine is provided. In one embodiment, selective histamine reuptake inhibitors are used. In some embodiments, therapeutic agents that up-regulate or down-regulate methyltransferase and/or diamine oxidase are used to decrease or increase endogenous histamine. Compositions that include methyltransferase and/or diamine oxidase, or agents with similar function, are provided in some embodiments.

In several embodiments, therapeutic agents that regulate endogenous GABA are provided, which in turn affects endogenous release of histamine. In one embodiment, histamine release is modulated by endogenous GABA through GABA-A and/or GABA-B receptors. In one embodiment, therapeutic agents that regulate GABA-B receptors or other receptors located on the histaminergic nerve terminals that modulate histamine release (e.g., pre-synaptically or post-synaptically) are provided.

In several embodiments, there is also provided a method of increasing histamine levels in a subject (e.g., a human patient) having a histamine level below a level required for optimum histamine function (as in histapenia), comprising administering a therapeutically effective amount of a therapeutic agent (e.g., histamine) to a subject according to the dosing regimens disclosed herein. As used herein, the term "therapeutically effective amount" shall be given its ordinary meaning and shall also include an amount of a therapeutic agent sufficient to elicit a desired biological response. Depending on the embodiment, the therapeutically effective amount may depend on the age, sex and weight of the patient, and/or the current medical condition of the patient.

In several embodiments, there is also provided a method for restoring histamine balance in a subject by normalizing activity of histamine receptors through multiple doses administered in successive therapy segments, comprising administering a first therapy segment, that first therapy segment comprising activating a histamine H3 receptor by administering to a subject a first dose of a histamine receptor activator, activating a histamine H4 receptor by administering to a subject a second dose of the histamine receptor activator, activating a histamine H1 receptor by administering to a subject a third dose of the histamine receptor activator, activating a histamine H2 receptor by administering to a subject a fourth dose of the histamine receptor activator, and administering a second therapy segment, comprising administering the histamine receptor activator in an amount greater than the amount administered in the first therapy segment, and administering a third therapy segment, comprising administering the histamine receptor activator in an amount greater than the amount administered in the second therapy segment. In additional embodiments, there is also provided a method for restoring histamine balance in a subject by normalizing activity of histamine receptors through multiple doses administered in successive therapy segments, comprising administering a first therapy segment, that first therapy segment comprising activating one or more of a histamine H3 receptor and a histamine H4 receptor by administering to a subject a first dose of a histamine receptor activator, activating a one or more of a histamine H3 receptor and a histamine H4 receptor by administering to a subject a second dose of the histamine receptor activator, activating a histamine H1 receptor by administering to a subject a third dose of the histamine receptor activator, activating a histamine H2 receptor by administering to a subject a fourth dose of the histamine receptor activator, and administering a second therapy segment, comprising administering the histamine receptor activator in an amount greater than the amount administered in the first therapy segment, and administering a third therapy segment, comprising administering the histamine receptor activator in an amount greater than the amount administered in the second therapy segment. In several embodiments, the increasing amount of the histamine receptor activator administered in each successive therapy segment suppresses activity of the histamine H1 receptor and enhances activity of a histamine receptor selected from the group consisting of the histamine H2, H3, and H4 receptors, thereby normalizing the activity of the histamine receptors and restoring histamine balance.

In several embodiments, there is also provided a method for restoring histamine balance in a subject by normalizing activity of histamine receptors through multiple doses administered in successive therapy segments, comprising administering a first therapy segment to the subject, the first segment comprising administering to a subject a first dose of a therapeutic agent that binds a histamine H3 receptor by administering to the subject a first dose of a therapeutic agent, administering to the subject a second dose of a therapeutic agent that binds a histamine H4 receptor by administering to the subject a second dose of the therapeutic agent, administering to the subject a first dose of a therapeutic agent that binds a histamine H1 receptor by administering to the subject a third dose of the therapeutic agent, administering to the subject a first dose of a therapeutic agent that binds a histamine H2 receptor by administering to the subject a fourth dose of the therapeutic agent, administering a second therapy segment to the subject, the second segment comprising administering the therapeutic agent in an amount greater than the amount administered in the first therapy segment, and administering a third therapy segment to the subject, the third segment comprising administering the therapeutic agent in an amount greater than the amount administered in the second therapy segment. Additionally, in several embodiments, there is also provided a method for restoring histamine balance in a subject by normalizing activity of histamine receptors through multiple doses administered in successive therapy segments, comprising administering a first therapy segment to the subject, the first segment comprising administering to a subject a first dose of a therapeutic agent that binds a histamine receptor selected from the group consisting of a histamine H3 receptor and a histamine H4 receptor by administering to the subject a first dose of a therapeutic agent, administering to the subject a second dose of a therapeutic agent that binds a histamine receptor selected from the group consisting of a histamine H3 receptor and a histamine H4 receptor by administering to the subject a second dose of the therapeutic agent, administering to the subject a first dose of a therapeutic agent that binds a histamine H1 receptor by administering to the subject a third dose of the therapeutic agent, administering to the subject a first dose of a therapeutic agent that binds a histamine H2 receptor by administering to the subject a fourth dose of the therapeutic agent, administering a second therapy segment to the subject, the second segment comprising administering the therapeutic agent in an amount greater than the amount administered in the first therapy segment, and administering a third therapy segment to the subject, the third segment comprising administering the therapeutic agent in an amount greater than the amount administered in the second therapy segment.

There is also provided, in several embodiments, methods for down-regulating a histamine H1 receptor comprising administering a first therapy segment, comprising administering to a subject a first dose of a therapeutic agent that binds a histamine H3 receptor administering to the subject a first dose of the therapeutic agent, administering to the subject a second dose of a therapeutic agent that binds a histamine H4 receptor by administering to the subject a second dose of the therapeutic agent, administering to the subject a first dose of a therapeutic agent that binds a histamine H1 receptor by administering to the subject a third dose of the therapeutic agent, administering to the subject a first dose of a therapeutic agent that binds a histamine H2 receptor by administering to the subject a fourth dose of the therapeutic agent, administering to the subject a second therapy segment, the second segment comprising administering the therapeutic agent in an amount greater than the amount administered in the first therapy segment, administering a third therapy segment to the subject, the third segment comprising: administering the therapeutic agent in an amount greater than the amount administered in the second therapy segment, wherein the increasing amount of the therapeutic agent administered in each successive therapy segment down-regulates activity of the histamine H1 receptor There is also provided, in several embodiments, methods for down-regulating a histamine H1 receptor comprising administering a first therapy segment, comprising administering to a subject a first dose of a therapeutic agent that binds a histamine receptor selected from the group consisting of a histamine H3 receptor and a histamine H4 receptor by administering to the subject a first dose of the therapeutic agent, administering to the subject a second dose of a therapeutic agent that binds a histamine receptor selected from the group consisting of a histamine H3 receptor and a histamine H4 receptor by administering to the subject a second dose of the therapeutic agent, administering to the subject a first dose of a therapeutic agent that binds a histamine H1 receptor by administering to the subject a third dose of the therapeutic agent, administering to the subject a first dose of a therapeutic agent that binds a histamine H2 receptor by administering to the subject a fourth dose of the therapeutic agent, administering to the subject a second therapy segment, the second segment comprising administering the therapeutic agent in an amount greater than the amount administered in the first therapy segment, administering a third therapy segment to the subject, the third segment comprising: administering the therapeutic agent in an amount greater than the amount administered in the second therapy segment, wherein the increasing amount of the therapeutic agent administered in each successive therapy segment down-regulates activity of the histamine H1 receptor. Optionally, additional therapy segments can be administered as well.

In several embodiments, the histamine receptor activator is administered in one or more of varied concentration (e.g., increased concentration as compared to a preceding administration), varied volume (e.g., increased concentration as compared to a preceding administration), or with a varied timing (e.g., the frequency of administration is reduced with successive segments). The tri-variable approach is beneficial in several embodiments, because cellular distribution and receptor contact can be adjusted. In this manner, selective activation of receptors can be achieved. Moreover, in several embodiments, the sequence of receptor activation can be altered depending on the condition being treated. For example, in several embodiments, a therapeutic agent can be administered at a dose sufficient to preferentially activate or bind an H1 receptor, and increase histamine levels in a subject (e.g., to treat histapenia). Alternatively, a therapeutic agent can be administered at a dose sufficient to preferentially activate or bind H2 and/or H3 receptor (which in several embodiments suppresses the activity and/or expression of the histamine H1 receptor and leads to reduction in histamine levels, such as when treating histadelia).

In several embodiments, the therapeutic agent and/or histamine receptor activator comprises histamine. In several embodiments, the histamine receptor activator comprises a histamine salt selected from the group consisting of histamine diphosphate, histamine phosphate, and histamine dihydrochloride. Combinations of these salts or other various salts of histamine may also be used, depending on the embodiment.

In several embodiments the successive therapy segments (e.g., the second, third, etc. therapy segment) comprises at least a first dose, a second dose, a third dose and a fourth dose of the histamine receptor activator. Optionally several embodiments comprise administering at least a fourth therapy segment, wherein the fourth therapy segment comprises administering the histamine receptor activator in an amount greater than the amount administered in the third therapy segment.

In several embodiments, the total dose of the histamine receptor activator in the first therapy segment ranges from about 100 ng to 700 ng, including about 200 ng to about 600 ng, about 300 ng to about 500 ng, about 400 ng, and overlapping ranges thereof. In several embodiments, the total dose of the histamine receptor activator in the second therapy segment ranges from about 600 ng to about 1000 ng, including about 600 ng to about 800 ng, about 650 ng to about 1000 ng, about 800 ng to about 1000 ng, and overlapping ranges therein. In several embodiments, the total dose of the histamine receptor activator in the third therapy segment ranges from about 1050 ng to about 1600 ng, including about 1050 ng to about 1200 ng, about 1200 ng to about 1300 ng, about 1300 ng to about 1400 ng, about 1400 ng to about 1500 ng, about 1500 ng to about 1600 ng, about 1050 ng to about 1500 ng and overlapping ranges thereof. In several embodiments, these doses are provided in varying volumes using a multi-variable approach, which in some embodiments, results in certain histamine receptors being activated to a greater degree than other histamine receptors. For example, the affinities in Table 1 are exploited in several embodiments of the invention to induce a targeted, sequenced and controlled histamine receptor activation pattern.

In several embodiments, the second therapy segment is longer in time than the first therapy segment and wherein the third therapy segment is longer in time than the second therapy segment. In embodiments wherein additional therapy segments are administered, successive therapy segments are optionally longer in duration than those preceding it (e.g., each successive segment is longer in duration). In several embodiments, the frequency of administration of the therapeutic agent (e.g., a histamine receptor activator) remains constant from segment to segment, such that the increased duration of successive segments reduces the administration frequency (as compared to the previous segment). By way of example, in several embodiments, the first therapy segment occurs over 10-16 days, the second therapy segment occurs over 20-35 days, and the third therapy segment occurs over 38-50 days. In additional embodiments, the first therapy segment is optionally administered on a compressed time-frame. For example, in several embodiments the doses comprising the first therapy segment are, in several embodiments, administered within a shortened time frame (e.g., about 30 seconds to about 5 minutes). As a result, the modulation of the various receptors occurs on a reduced time-frame, and in some embodiments, simultaneously. In such embodiments, the first therapy segment advantageously "jump-starts" the regimen by concurrent receptor modulation. In several embodiments, the first therapy segment comprises simultaneously delivery of each of the doses within the segment. In several embodiments, the first therapy segment is compressed to occur over about 1-2 minutes, about 2-3 minutes, about 3-4 minutes, about 4-5 minutes, about 5-10 minutes, about 10-20 minutes, about 20-30 minutes, and overlapping ranges thereof.

In several embodiments, the administration of the therapeutic agent (e.g., a histamine receptor activator) comprises subcutaneous injection of histamine or a histamine salt, wherein the total dose of the first therapy segment is about 200 ng to about 600 ng, wherein the total dose of the second therapy segment is about 650 ng to about 1000 ng, wherein the total dose of the third therapy segment is about 1050 ng to about 1500 ng, wherein the second therapy segment is longer than the first therapy system, and wherein the third therapy segment is longer than the second therapy system.

In additional embodiments, administration of the therapeutic agent (e.g., a histamine receptor activator) comprises intravenous injection. In still further embodiments, the therapeutic agent (e.g., a histamine receptor activator) is administered by an oral delivery route. In still further embodiments, the therapeutic agent (e.g., a histamine receptor activator) is administered by inhalation. In still further embodiments, the therapeutic agent (e.g., a histamine receptor activator) is administered through a transdermal patch. In several embodiments, the administration of the therapeutic agent (e.g., a histamine receptor activator) comprises a route selected from the group consisting of subcutaneous, intraarterial, intravenous, and combinations thereof. Depending on the embodiment, a given segment may be delivered by a first route of administration (e.g., subcutaneous), while another segment is delivered by a different route (e.g., oral). In several embodiments, modification of the administration route reduces risk of side effects associated with a single administration route. Moreover, in several embodiments, the change in administration route enables a greater proportion of the histamine receptors in certain organ banks to be reached. For example, oral administration may facilitate restoration of balance of histamine receptor activity in the gastrointestinal tract to a greater degree than intravenous administration. In several embodiments, the therapeutic agent is delivered by a non-invasive administration route. In several embodiments, the therapeutic agent is self-administered. In several embodiments, the therapeutic agent is administered by, for example, a nurse, a physician, a hospice care worker, and/or another medical provider, while in some embodiments, the therapeutic agent is administered by a an individual who is not a medical professional (e.g., a non-medical professional, such as, for example, an acquaintance, family member, spouse, etc.).

In several embodiments, the subject receiving therapy is susceptible to migraine headaches and the restored histamine balance leads to a reduction in duration, frequency and/or intensity of migraine headaches.

In several embodiments, the subject receiving therapy has histadelia and the restored histamine balance treats the histadelia. In several embodiments, the subject receiving therapy has histapenia and the restored histamine balance treats the histapenia.

In several embodiments, therapeutic agent (e.g., a histamine receptor activator) is provided as a liquid formulation. In several embodiments, the first dose of the histamine receptor activator in the first therapy segment has a concentration ranging from between about 0.1 pg/mL to about 10 pg/mL, including about 0.5 pg/mL, about 1 pg/mL, about 2 pg/mL, about 3 pg/mL, about 4 pg/mL, about 5 pg/mL, about 6 pg/mL, about 7 pg/mL, about 8 pg/mL, about 9 pg/mL, about 10 pg/mL, and concentrations therebetween.

In several embodiments, the second dose of the histamine receptor activator in the first therapy segment has a concentration ranging from between about 0.1 ng/mL to about 10 ng/mL, including about 0.5 ng/mL, about 1.0 ng/mL, about 2 ng/mL, about 3 ng/mL, about 4 ng/mL, about 5 ng/mL, about 6 ng/mL, about 7 ng/mL, about 8 ng/mL, about 9 ng/mL, about 10 ng/mL, and concentrations therebetween.

In several embodiments, the third dose of the histamine receptor activator in the first therapy segment has a concentration ranging from between about 0.1 μg/mL to about 2.999 μg/mL (e.g., about 0.1 μg/mL to about 2.999 μg/mL), including about 0.1 μg/mL, about 0.5 μg/mL, about 1 μg/mL, about 1.5 μg/mL, about 2 μg/mL, about 2.5 μg/mL, about 2.999 μg/mL, and concentrations therebetween. In several embodiments, the third dose of the histamine receptor activator in the first therapy segment has a concentration ranging from between about 0.1 μg/mL to about 3.49 μg/mL, including about 0.1 μg/mL, about 0.5 μg/mL, about 1 μg/mL, about 1.5 μg/mL, about 2 μg/mL, about 2.5 μg/mL, about 3 μg/mL, about 3.49 μg/mL, and concentrations therebetween.

In several embodiments, the fourth dose of the histamine receptor activator in the first therapy segment has a concentration ranging from between about 3.0 μg/mL to about 10 μg/mL, including about 3 μg/mL, about 3.5 μg/mL, about 4 μg/mL, about 4.5 μg/mL, about 5 μg/mL, about 6 μg/mL, about 7 μg/mL, about 8 μg/mL, about 9 μg/mL, about 10 μg/mL, and concentrations therebetween. In several embodiments, the fourth dose of the histamine receptor activator in the first therapy segment has a concentration ranging from between about 0.35 μg/mL to about 10 μg/mL, including about 0.35 μg/mL, about 0.75 μg/mL, about 1 μg/mL, about 1.5 μg/mL, about 2 μg/mL, about 2.5 μg/mL, about 3 μg/mL, about 3.5 μg/mL, about 4 μg/mL, about 4.5 μg/mL, about 5 μg/mL, about 6 μg/mL, about 7 μg/mL, about 8 μg/mL, about 9 μg/mL, about 10 μg/mL, and concentrations therebetween.

In several embodiments, the volume of each dose in the first therapy segment ranges from between about 0.01 mL to about 1.0 mL, including about 0.1 mL, about 0.5 mL, about 0.75 mL, about 1 mL, and volumes therebetween. In several embodiments, the histamine receptor activator is administered with a frequency of between one and three times per week during the first therapy segment, such as, for example, two times per week during the first therapy segment.

In several embodiments, the second therapy segment comprises a first dose, a second dose, a third dose, and a fourth dose, and the first dose in the second therapy segment has a concentration ranging from between about 0.1 pg/mL to about 10 pg/mL (e.g., about 0.1 pg/mL, about 1 pg/mL, about 5 pg/mL, about 10 pg/mL and concentrations therebetween). In several embodiments, the second dose in the second therapy segment has a concentration ranging from between about 0.1 ng/mL to about 10 ng/mL (e.g., about 0.5 ng/mL, about 1.0 ng/mL, about 5 ng/mL, about 10 ng/mL, and concentrations therebetween). In several embodiments, the third dose in the second therapy segment has a concentration ranging from between about 0.1 μg/mL to about 2.999 μg/mL (e.g., about 0.1 μg/mL, about about 1 μg/mL, about 2 μg/mL, about 2.5 μg/mL, about 2.999 μg/mL, and concentrations therebetween). In several embodiments, the fourth dose in the second therapy segment has a concentration ranging from between about 3.0 μg/mL to about 10 μg/mL (e.g., about 3.0 μg/mL, about 3.5 μg/mL, about 4 μg/mL, about 4.5 μg/mL, about 6 μg/mL, about 8 μg/mL, about 10 μg/mL, and concentrations therebetween). In additional embodiments, the third dose in the second therapy segment has a concentration ranging from between about 0.1 μg/mL to about 3.49 μg/mL (e.g., about 0.1 μg/mL, about 1 μg/mL, about 2 μg/mL, about 3 μg/mL, about 3.49 μg/mL, and concentrations therebetween). In several embodiments, the fourth dose in the second therapy segment has a concentration ranging from between about 0.35 μg/mL to about 10 μg/mL (e.g., about 0.35 μg/mL, about 1 μg/mL, about 1.5 μg/mL, about 3 μg/mL, about 3.5 μg/mL, about 4 μg/mL, about 4.5 μg/mL, about 6 μg/mL, about 8 μg/mL, about 10 μg/mL, and concentrations therebetween).

In several embodiments, the volume of each dose in the second therapy segment ranges from between about 0.02 mL to about 2.0 mL, such as, for example, about 0.2 mL, about 0.5 mL, about 0.75 mL, about 1 mL, about 1.5 mL, about 2 mL and volumes therebetween.

In several embodiments, the second segment comprises administration of the histamine receptor activator with a frequency of between 2 times per week and once every 10 days during the second therapy segment, such as, for example, once per week, twice, per week, once every eight days, once every ten days, and frequencies therebetween.

In several embodiments, the third therapy segment comprises a first dose, a second dose, a third dose, and a fourth dose, and the first dose in the third therapy segment has a concentration ranging from between about 0.1 pg/mL to about 10 pg/mL (e.g., about 0.1 pg/mL, about 1 pg/mL, about 5 pg/mL, about 10 pg/mL and concentrations therebetween). In several embodiments, the second dose in the third therapy segment has a concentration ranging from between about 0.1 ng/mL to about 10 ng/mL (e.g., about 0.5 ng/mL, about 1.0 ng/mL, about 5 ng/mL, about 10 ng/mL, and concentrations therebetween). In several embodiments, the third dose in the third therapy segment has a concentration ranging from between about 0.1 µg/mL to about 2.999 µg/mL (e.g., about 0.1 µg/mL, about about 1 µg/mL, about 2 µg/mL, about 2.999 µg/mL, and concentrations therebetween). In several embodiments, the fourth dose in the third therapy segment has a concentration ranging from between about 3.0 µg/mL to about 10 µg/mL (e.g., about 3 µg/mL, about 3.5 µg/mL, about 4 µg/mL, about 4.5 µg/mL, about 6 µg/mL, about 8 µg/mL, about 10 µg/mL, and concentrations therebetween). In several embodiments, the third dose in the third therapy segment has a concentration ranging from between about 0.1 µg/mL to about 3.49 µg/mL (e.g., about 0.1 µg/mL, about 1 µg/mL, about 2 µg/mL, about 3 µg/mL, about 3.49 µg/mL, and concentrations therebetween). In several embodiments, the fourth dose in the third therapy segment has a concentration ranging from between about 0.35 µg/mL to about 10 µg/mL (e.g., about 0.35 µg/mL, about 1 µg/mL, about 1.5 µg/mL, about 3 µg/mL, about 3.5 µg/mL, about 4 µg/mL, about 4.5 µg/mL, about 6 µg/mL, about 8 µg/mL, about 10 µg/mL, and concentrations therebetween).

In several embodiments, the volume of each dose in the third therapy segment ranges from between about 0.03 mL to about 3.0 mL, such as, for example, about 0.3 mL, about 0.5 mL, about 0.75 mL, about 1 mL, about 2.0 mL, about 3.0 mL and volumes therebetween.

In several embodiments, the third segment comprises administration of the histamine receptor activator with a frequency of between once per week and once every two weeks during the third therapy segment, such as, for example, once per week, once every eight days, once every ten days, once every twelve days, once every fourteen days, and frequencies therebetween.

Additionally, there are provided, in several embodiments, methods for reducing, ameliorating, preventing, and/or inhibiting the frequency, duration and/or intensity of migraine headaches in a subject through normalization of the activity and/or expression of one or more histamine receptors, comprising identifying a subject susceptible to migraine headaches and having a histamine imbalance, administering to the subject a first histamine dosing segment comprising a first, a second, a third, and a fourth dose of histamine, wherein the first dose is administered subcutaneously at a concentration between about 0.1 pg/mL to about 10 pg/mL and activates a histamine receptor selected from the group consisting of a histamine H3 receptor and a histamine H4 receptor, wherein the second dose of histamine is administered subcutaneously at a concentration between about 0.1 ng/mL to about 10 ng/mL and activates a histamine receptor selected from the group consisting of a histamine H3 receptor and a histamine H4 receptor, wherein the third dose of histamine is administered subcutaneously at a concentration between about 0.1 µg/mL to about 3.49 µg/mL (for example, between about 0.1 µg/mL to about 2.999 µg/mL) and activates a histamine H1 receptor, wherein the fourth dose of histamine is administered subcutaneously at a concentration between about 0.35 µg/mL to about 10 µg/mL (for example, about 3.0 µg/mL to about 10 µg/mL) and activates a histamine H2 receptor, wherein each dose in the first dosing segment has the same volume and wherein the volume ranges from between about 0.01 mL to about 1.0 mL, wherein each successive dose comprises a larger amount of histamine as compared to the preceding dose; administering to the subject a second histamine dosing segment comprising a first, a second, a third, and a fourth dose of histamine, wherein the concentration of the histamine administered in each dose is equivalent to the corresponding concentration of histamine each dose of the first dosing segment, wherein each dose in the second dosing segment has the same volume, and wherein the volume ranges from between about 0.02 mL to about 2.0 mL, wherein the total amount of histamine delivered in the second dosing segment is greater than the amount delivered in the first dosing segment; and administering to the subject a third histamine dosing segment comprising a first, a second, a third, and a fourth dose of histamine, wherein the concentration of the histamine administered in each dose is equivalent to the corresponding concentration of histamine each dose of the first dosing segment, wherein each dose in the third dosing segment has the same volume, and wherein the volume ranges from between about 0.03 mL to about 3.0 mL, wherein the total amount of histamine delivered in the third dosing segment is greater than the amount delivered in the second dosing segment. In several embodiments, the increase in the amount of histamine administered with each successive dosing segment suppresses activity of the H1 receptor and enhances activity of the H2, H3 and/or H4 receptors, thereby normalizing the activity and/or expression of the histamine receptors and reducing the duration, frequency and/or intensity of migraine headaches in the subject.

In several embodiments, the ratio of individual doses within any of the first, second, or third therapy segment is $1:10^3:10^6:3.5\times10^6$. As discussed above, these ratios (either by adjustment of volume or concentration) can be adjusted if a subject requires an increase or a decrease in histamine activity (or receptor expression). The methods also optionally include administration of an additional agonist or an antagonist of any of the histamine H1, H2, H3, or H4 receptors. Moreover, the methods, in several embodiments, include one or more of identifying a subject having histamine imbalance (such as for example, but measuring the serum and/or urine histamine concentrations) and instructing administration of the therapeutic agent.

There are also provided herein histamine receptor activators for use in up-regulating certain histamine receptors and down-regulating other histamine receptors to balance the histamine system, which in turn may be useful for the treatment of migraine headaches, Parkinson's Disease, Alzheimer's Disease, coronary disease, leukemia, amyotrophic lateral sclerosis, epilepsy histadelia and/or histapenia and other disorders. In several embodiments, there is additionally provided a histamine receptor activator(s) for use in the treatment of migraine headaches, Parkinson's Disease, Alzheimer's Disease, coronary disease, leukemia, amyotrophic lateral sclerosis and/or epilepsy, histadelia and/or histapenia by administration of a dosage of the activator divided into at least three therapy segments, wherein the total dose of the histamine receptor activator in the first therapy segment is about 200 ng to about 600 ng, wherein the total dose of the histamine receptor activator in the second therapy segment is about 650 ng to about 1000 ng, and wherein the total dose of the histamine receptor activator in the third therapy segment is about 1050 ng to about 1500 ng.

There is also provided a histamine receptor activator for use in the treatment of migraine headaches by subcutaneous administration of said histamine receptor activator. In several embodiments, the histamine receptor activator comprises histamine, and/or a histamine salt selected from the group consisting of one or more of histamine diphosphate, histamine phosphate, and histamine dihydrochloride.

Also provided herein is a histamine receptor activator (or activators) for use in the treatment of migraine headaches, Parkinson's Disease, Alzheimer's Disease, coronary disease, leukemia, amyotrophic lateral sclerosis epilepsy, histadelia and/or histapenia (or other ailments) in patients showing an elevated amount of circulating histamine as well as ailments in which patients show a reduced amount of circulating histamine. Thus, in several embodiments, the invention comprises a histamine receptor activator for regulating endogenous histamine levels, including but not limited to use in the treatment of migraine headaches, Parkinson's Disease, Alzheimer's Disease, coronary disease, leukemia, amyotrophic lateral sclerosis, epilepsy, histadelia and/or histapenia to restore histamine balance in the subject.

In several embodiments, the invention comprises a histamine receptor activator (or activators) for use in the treatment of migraine headaches, Parkinson's Disease, Alzheimer's Disease, coronary disease, leukemia, amyotrophic lateral sclerosis, epilepsy, histadelia and/or histapenia by inhibiting the activity and/or expression of a histamine receptor selected from the group consisting of the histamine H1 receptor, the histamine H2 receptor, the histamine H3 receptor, and the histamine H4 receptor. In several embodiments, the histamine receptor activator inhibits the activity and/or expression of the histamine H1 receptor.

In several embodiments, the invention comprises a histamine receptor activator for use in the treatment of diseases associated with the over-expression and/or over-activity of the histamine H1 receptor, such as, for example, one or more of migraine headaches, Parkinson's Disease, Alzheimer's Disease, coronary disease, leukemia, amyotrophic lateral sclerosis epilepsy, histadelia and/or histapenia. Similarly, there is provided, in several embodiments, a histamine receptor activator for use in the treatment of diseases associated with the under-expression and/or under-activity one or more of the histamine H2, H3, and/or H4 receptors, such as, for example, migraine headaches, Parkinson's Disease, Alzheimer's Disease, coronary disease, leukemia, amyotrophic lateral sclerosis, epilepsy, histadelia and/or histapenia.

In several embodiments, the invention comprises, a histamine receptor activator(s) for use in the treatment of migraine headaches, Parkinson's Disease, Alzheimer's Disease, coronary disease, leukemia, amyotrophic lateral sclerosis, epilepsy, histadelia and/or histapenia by combined, sequential, or separate administration with a complete or partial antagonist of a histamine H1 receptor.

In several embodiments, the invention comprises an inhibitor of the activity and/or expression of a histamine H1 receptor for use in the treatment of migraine headaches, Parkinson's Disease, Alzheimer's Disease, coronary disease, leukemia, amyotrophic lateral sclerosis, epilepsy, histadelia and/or histapenia.

Additionally provided herein is an escalating histamine dosing regimen comprising a first dosing segment comprising two or more sequential doses of histamine separated by a first time interval, wherein the doses increase in histamine concentration from dose to dose while the administered volume of each dose stays constant and a second dosing segment comprising two or more sequential doses of histamine separated by a second time interval, wherein the doses increase in histamine concentration from dose to dose while the administered volume of each dose stays constant wherein the volume of each histamine dose in the second dosing segment is greater than the volume of each histamine dose in the first dosing segment, and the second time interval is longer than the first time interval. In several embodiments, the first dosing segment comprises a first, a second, a third, and a fourth dose. In some such embodiments, the first dose is administered subcutaneously at a concentration of 1.1 ng/mL+/−20-30% and activates a histamine H3 receptor, the second dose of histamine is administered subcutaneously at a concentration of 3 ng/mL+/−40-50% and activates a histamine H4 receptor, the third dose of histamine is administered subcutaneously at a concentration of 1.1 µg/mL+/−20-30% and activates a histamine H1 receptor, and the fourth dose of histamine is administered subcutaneously at a concentration of 3.33 µg/mL+/−20-30% and activates a histamine H2 receptor.

In several embodiments of the histamine dosing regimen, the concentrations of histamine administered during the first dosing segment are the same as the concentrations of histamine administered during the second dosing segment, the number of doses administered during the first dosing segment is equal to the number of doses administered during the second dosing segment, the first dosing segment and the second dosing segment are separated by the first time interval.

Optionally, the histamine dosing regimen may further comprise a third dosing segment comprising two or more sequential doses of histamine separated by a third time interval, wherein the doses increase in histamine concentration from dose to dose while the administered volume of each dose stays constant, the volume of each dose in the third dosing segment is greater than the volume of each dose administered in the second dosing segment, and the third time interval is longer than the second time interval. In such, embodiments, the concentrations of histamine administered during the third dosing segment are the same as the concentrations of histamine administered during the second dosing segment, the number of doses administered during the third dosing segment is equal to the number of doses administered during the second dosing segment, and the second dosing segment and the third dosing segment are separated by the second time interval.

Depending on the embodiment, each dosing segment may comprise three or more doses, for example, in some embodiments, each dosing segment comprises four doses, five doses, six doses, eight doses, or ten doses.

As discussed herein, there are also provided, in several embodiments, extended duration regimens, such as those comprising up to ten (or more) sequential dosing segments, wherein each dosing segment comprises two or more sequential doses of histamine separated by one or more equal time intervals, the doses in each segment increase in histamine concentration from dose to dose while the administered volume of each dose stays constant, the volume of each histamine dose in a succeeding dosing segment is greater than the volume of each histamine dose in the preceding dosing segment, the time interval in each succeeding dosing segment is longer than the time interval in the preceding dosing segment, the concentrations of histamine administered are the same in each dosing segment, the number of doses administered during each segment is equal, and/or each succeeding dosing segment is separate from the immediately preceding dosing segment by the time interval observed for the immediately preceding dosing segment.

For example, in some extended dosing regimen embodiments comprising ten dosing segments, the volume per dose in the first segment is about 0.1 mL and the volume of each dose in each succeeding segment is about 0.1 mL greater than the volume administered in the immediately preceding segment.

In several embodiments, the histamine concentration of each dose in each segment ranges from about 1 attogram/ml to 20 µg/ml, such as for example concentrations ranging (for each dose) from about 1 pg/ml to about 3.5 µg/ml. (or, as in one embodiment, 1 pg/ml to about 2.999 µg/ml). In several embodiments, the first dosing interval ranges from about one day to one week in duration, and the second dosing interval ranges from about three days to two weeks in duration. Subsequent dosing intervals, in several embodiments, successively increase in duration, such as for example, a third dosing interval may range from about one week to about three weeks.

Depending on the embodiment, histamine used in the histamine dosing regimen can be present as a free base, a pharmaceutically acceptable salt thereof, or combinations thereof. Depending on the embodiments, the route of administration is via subcutaneous, intravenous, intra-muscular, infusion, transdermal, inhalation and/or sub-lingual administration.

There are also provided herein methods for lowering histamine levels in a human patient having a histamine level above a level required for optimum histamine function, comprising administering histamine or a pharmaceutically acceptable salt thereof to the patient according to the dosing regimens described herein. A method of increasing histamine levels in a human patient having a histamine level below a level required for optimum histamine function, comprising administered histamine or a pharmaceutically acceptable salt thereof to the patient according to the dosing regimens described herein. In several embodiments, the assessment of the level of histamine required for optimum histamine function is based on plasma histamine levels or urine histamine levels, and diagnostic tests for measuring same. In several embodiments, the level required for optimum histamine function is between about 45 and about 50 ng/ml of plasma. However, in several embodiments, restoration of histamine levels to a level above or below that range, but to a concentration that is normal for a particular individual, is achieved.

In several embodiments, a method for restoring histamine balance is provided. In some embodiments, normalizing activity of histamine receptors is achieved through administration of (or instructing the administration of) multiple doses of a histamine receptor activator administered in successive therapy segments. In several embodiments, the methods comprise administering at least a first, a second, and a third initial therapy segments, each of the initial segments comprising activating a histamine H3 or H4 receptor by administering to a subject a first dose of a histamine receptor activator, activating a histamine receptor by administering to a subject a second dose of the histamine receptor activator, activating a histamine H2 receptor by administering to a subject a third dose of the histamine receptor activator, and administering a plurality of escalating therapy segments, each of the escalating therapy segments comprising activating a histamine H3 or H4 receptor by administering to a subject a first dose of the histamine receptor activator, activating a histamine H1 receptor by administering to a subject a second dose of the histamine receptor activator, activating a histamine H2 receptor by administering to a subject a third dose of the histamine receptor activator thereby normalizing the activity of the histamine receptors and restoring histamine balance.

In several additional embodiments, a method for restoring histamine balance is provided, the method comprising normalizing activity of histamine receptors through multiple doses administered in successive therapy segments. In several embodiments normalization of receptor activity is accomplished by administering, or instructing the administration of, at least a first, a second, and a third initial therapy segments, each of the initial segments comprising activation of a histamine H3 receptor by administering to a subject a first dose of a histamine receptor activator, activation of a histamine H4 receptor by administering to a subject a second dose of a histamine receptor activator, activation of a histamine H1 receptor by administering to a subject a third dose of the histamine receptor activator, activation of a histamine H2 receptor by administering to a subject a fourth dose of the histamine receptor activator, administering, or instructing the administration of, a plurality of escalating therapy segments, each of the escalating therapy segments comprising activation of a histamine H3 receptor by administering to a subject a first dose of the histamine receptor activator, activation of a histamine H4 receptor by administering to a subject a second dose of the histamine receptor activator, activation of a histamine H1 receptor by administering to a subject a third dose of the histamine receptor activator, activation of a histamine H2 receptor by administering to a subject a fourth dose of the histamine receptor activator. In several embodiments, the amount of the histamine receptor activator in the second initial therapy segment is greater than the amount of the histamine receptor activator in the first initial therapy segment, the amount of the histamine receptor activator in the third initial therapy segment is greater than the amount of the histamine receptor activator in the second initial therapy segment, the amount of the histamine receptor activator administered in each successive escalating therapy segment is greater than the preceding escalating therapy segment, and the increasing of amount histamine receptor activator administered enhances activity of a histamine receptor selected from the group consisting of the histamine H1, H2, H3, and H4 receptors, thereby normalizing the activity of the histamine receptors and restoring histamine balance.

In several embodiments, the amount of the histamine receptor activator in the second initial therapy segment is greater than the amount of the histamine receptor activator in the first initial therapy segment and the amount of the histamine receptor activator in the third initial therapy segment is greater than the amount of the histamine receptor activator in the second initial therapy segment. In those embodiments where additional initial therapy segments are administered, the amount of the histamine receptor activator administered in each successive initial therapy segment is greater than the preceding segment. In several embodiments, the amount of the histamine receptor activator administered in each successive escalating therapy segment is greater than the preceding escalating therapy segment. In several embodiments, the wherein the increasing of amount histamine receptor activator administered leads to suppression of the activity of the histamine H1 receptor, but enhances activity of a histamine receptor selected from the group consisting of the histamine H2, H3, and H4 receptors, thereby normalizing the activity of the histamine receptors and restoring histamine balance.

There is provided a method for restoring histamine balance in a subject by normalizing activity of histamine receptors through an escalating dosing regimen, comprising administering a plurality of therapy segments, each of the segments comprising activating a histamine H3 receptor or H4 receptor by administering to a subject a first dose of a histamine receptor activator, activating a histamine H1 receptor by administering to a subject a second dose of the histamine receptor activator, activating a histamine H2 receptor by administering to a subject a third dose of the histamine receptor activator, wherein the amount of the histamine receptor activator administered in each successive escalating therapy segment is greater than the preceding escalating therapy segment, and wherein the increasing of amount histamine receptor activator administered leads to suppression of the activity of the histamine receptor while the activity of a histamine receptor selected from the group consisting of the histamine H2, H3, and H4 receptors is enhanced, resulting in a normalization of the activity of the histamine receptors and restoring histamine balance.

In several embodiments, the first dose, the second dose, and the third dose in each escalating therapy segment is administered within a total time frame of less than about 5 minutes, (e.g., less than 4 minutes, less than 3 minutes, less than 2 minutes, less than 1 minute).

In several embodiments, the histamine receptor activator comprises histamine. In additional embodiments, the histamine receptor activator comprises a histamine salt selected from the group consisting of histamine diphosphate, histamine phosphate, and histamine dihydrochloride.

In several embodiments, the administration of the histamine receptor activator comprises subcutaneous injection.

Also provided herein is a kit comprising formulations suitable for achieving the histamine normalization methods disclosed herein. In several embodiments, the invention comprises a kit (or dosing regimen) comprising formulations in concentrations set forth on any one of Tables 2-7.

In several embodiments, there is a provided a method of restoring histamine balance, comprising providing at least one histamine receptor activator and instructing the administration of the composition at concentrations suitable for activating one or more of the histamine H1, H2, H3, and/or H4 receptors. In several embodiments, the method further comprises providing an additional therapeutic composition that can either agonize or antagonize on or more of the histamine H1, H2, H3, and/or H4 receptors. In several embodiments, the at least one histamine receptor activator is histamine or a histamine salt. In several embodiments the at least one histamine receptor activator is provided as a concentrated composition (e.g., a liquid or a solid, such as a lyophilized powder) and is suitable for dilution into various concentrations that are used to specifically target one or more of the histamine receptors.

The methods summarized above and set forth in further detail below describe certain actions taken by a practitioner; however, it should be understood that they can also include the instruction of those actions by another party. Thus, actions such as "administering a histamine agonist" include "instructing the administration of a histamine agonist."

BRIEF DESCRIPTION OF THE DRAWINGS

FIG. 6 depicts a summary of previous clinical data related to brain histamine levels in patients with Parkinson's disease versus healthy subjects FIG. 7 depicts a summary of previous clinical data related to brain histamine concentration in patients with Alzheimer's disease versus healthy subjects FIG. 8 depicts a summary of previous clinical data related to histamine blood concentration in patients with coronary disease versus healthy subjects FIG. 9 depicts a summary of previous clinical data related to plasma histamine levels in patients with Myelogenous Leukemia versus healthy subjects

DETAILED DESCRIPTION

Several embodiments of the invention employ a multi-variable approach to treat imbalances of the histamine system. The multi-variable approach, which includes altering concentration, volume, and timing in some embodiments, may advantageously affect in vivo distribution to achieve selective (or enhanced) activation of certain histamine receptors. By employing a targeted and controlled pattern of receptor activation, receptors can be up and/or down regulated to rebalance the histamine system and offer profound relief for those who suffer from dysregulation of the histamine system.

General

Histamine, first identified as an autacoid having vasoactive properties, and also referred to in some contexts as "substance H", is a member of the biogenic amines family and is synthesized from the amino acid histidine by the activity of L-histidine decarboxylase (HDC). Histadine decarboxylase (HDC) is an enzyme that is expressed in various cells throughout the body, including central nervous systems (neurons), gastric-mucosa (parietal cells), mast cells (which can contain ~3 pg of histamine per cell), and basophils (which can contain ~1 pg of histamine per cell). Histamine is involved in a variety of different physiological functions, including but not limited to, immune and allegoric responses, endocrine system function and homeostasis as well as cell proliferation, differentiation hematopoiesis, embryonic development, regeneration, wound healing, aminergic neurotransmission, various other brain functions (sleep, nociception, food intake and aggressive behavior), secretion of pituitary hormones, regulation of gastrointestinal and cardiovascular systems, and other various signaling pathways. Histamine has also been correlated with allergies (e.g., drug allergies, hay fever, allergic asthma, etc.). Elevated histamine has also been detected in skin and plasma samples from patients with atopic dermatitis (AD), chronic urticaria (CU), multiple sclerosis (MS) and/or psoriatic skin. In Parkinson's Disease patients, histamine levels have been shown to be increased in specific brain regions, such as the putamen, substantia nigra and external globus pallidus. In Alzheimer's disease, certain histaminergic neurons display degeneration and tangle formation. Also, a decline in histamine levels and/or HDC activity has been associated with Alzheimer's disease and Down's syndrome.

Figure 1:
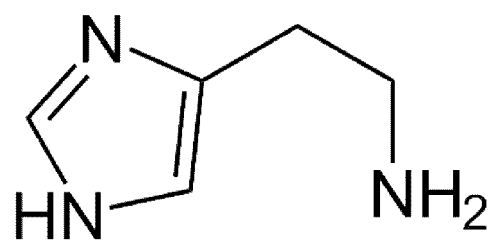
FIG. 1 depicts the chemical structure of histamine.
Figure 2:
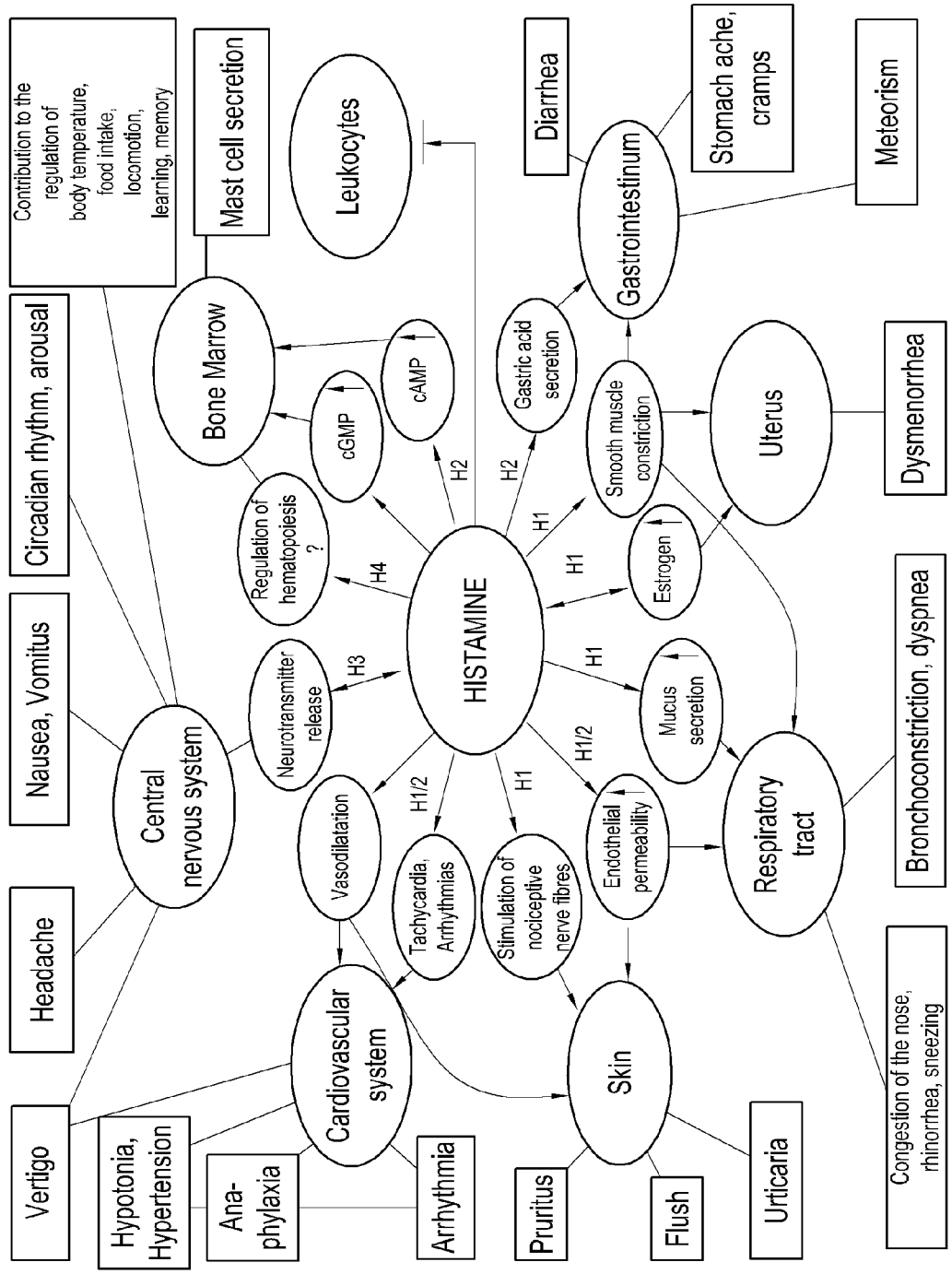
FIG. 2 depicts a schematic of various signaling pathways in which histamine plays a role and examples of symptoms that can result from the activity of histamine receptors in certain tissues.

Histamine is synthesized by a variety of cells, including, but not limited to mast cells, basophils, platelets, histaminergic neurons, and enterochromaffin cells. The activity of HDC is modulated by various cytokines, including inflammatory cytokines such as interleukin (IL)-1, IL-3, IL-12, IL-18 and tumor necrosis factor (TNF). Histamine is stored intracellularly in vesicles and released by particular stimuli, such as stress, circadian rhythms, drugs and allergens. Mast cells are relatively widely distributed throughout the body and the population density of mast cells is very high in anatomical sites which interface with the external environment (e.g., skin, airways, and gastrointestinal tract) as well as regions in close proximity to blood vessels, nerves, smooth muscle cells, epithelial cells, mucus producing cells and hair follicles. Given that histamine is stored in granules in a "ready to release" fashion, substantial amounts of preformed histamine can be released in response to a single stimulus, and a multitude of various triggers can elicit large-scale and rapid-onset histamine release (e.g., via mast cell degranulation), mast cells are a major cellular source of histamine. For example, in allergic reactions, for example, histamine is released from basophils and/or mast cells in response to particular allergens. Histamine mediates numerous biologic reactions, such as, for example, immune responses (e.g., inflammatory reactions, modulation of the immune response) and the degranulation of mast cells after their recognition of specific allergens. Histamine-induced signaling also plays a role in responses to many other nonimmunologic stimuli, such as, for example, neuropeptides, complement factors, cytokines, hyperosmolarity, lipoproteins, adenosine, superoxidases, hypoxia, reactions with certain drugs, peptides, venom, and/or other "liberators", physical insults (such as, for example, thermal, vibratory, radiant, or exertion), stressors (such as, for example, chemical, thermal, traumatic, or osmotic stressors), alcohol and certain food and drugs that may activate mast cells, and/or spontaneous basophil release (which occurs with higher frequency in atopic individuals). Allergic reactions such as, for example, excessive sneezing, are potentiated by the activation of histamine-based pathways because histamine also dilates blood vessels and increases permeability of vessel walls, thereby allowing potentially greater influx of allergens. FIG. 2 (reproduced with permission from Maintz, et al., *Histamine and Histamine Intolerance*, The American Journal of clinical Nutrition, Vol. 85: 1185-1196 (2007)) depicts the variety of different pathways in which histamine signaling plays a role, and examples of symptoms that may arise from dysregulation of histamine. As a result of the multitude of tissues in which histamine signaling occurs, dysregulation of histamine function can present with confounding symptoms (e.g., those not necessarily directly associated with a particular organ system, for example vertigo as a result of histamine dysregulation in the cardiovascular system). As such, several embodiments of the methods and compositions (and uses thereof) disclosed herein for restoration of histamine balance are particularly useful for amelioration (or elimination) of symptoms of histamine dysregulation in one or more tissues or tissue types.

Certain individuals are either sensitized to, or intolerant of, histamine. As discussed above, histamine is produced from L-histidine. Imbalance in the accumulation (e.g., production) and reduction (e.g., degradation and/or metabolism) can lead to the sensitization and or intolerance to histamine. The primary enzyme for metabolism of ingested histamine is diamine oxidase (DAO). Reduced histamine degradation based on insufficient DAO activity and can result in excess histamine and may cause symptoms mimicking allergic reactions. DAO is located in plasma membrane-associated vesicular structures and is secreted into the bloodstream after stimulation. The second major enzyme for metabolism of histamine is histamine-N-methyltransferase (HNMT), which is a cytosolic protein, and is therefore only capable of metabolizing intracellular histamine. Notwithstanding their differing, and seemingly non-competitive locations, reduced function of one or both of the enzymes can lead to histamine imbalance and/or sensitization to or intolerance of histamine. As discussed above, such imbalances can lead to a variety of adverse physiological consequences, and several embodiments of the methods disclosed herein restore histamine balance through the administration of a therapeutic agent (e.g., histamine).

Endogenous histamine acts on a large variety of different cell types including smooth muscle, neurons, endocrine and exocrine cells, blood cells and cells of the immune system. Histamine exerts its multiple biological actions via one of several receptors including the H1 receptor (H1R), H2 receptor (H2R), H3 receptor (H3R) and more recently, H4 receptors (H4R). Each of the receptors is a G protein coupled receptor, though they operate through various G-protein subunits and are differentially expressed in various cell types. The receptors have been detected in various tissues, including but not limited to, mammalian brain, respiratory tract, genito-urinary system and vascular system, as well as on several types of leukocytes and hematopoietic cells. The H1 receptors are mainly involved in the regulation of vascular permeability and smooth muscle contraction. The H2 receptor stimulation evokes an increase of gastric acid secretion, an increase in mucus secretion in the bronchi and the relaxation of smooth muscles of small blood vessels. The H3 receptors are classified as presynaptic receptors controlling neurotransmission in the central nervous system. H4 receptor signaling appears to modulate immune system processes and inflammatory reactions. It is believed that the principal receptors throughout the body are the H1 and H2 receptors, while H3 and H4 receptors have somewhat more localized expression profiles. In some instances, histamine signaling through H1R and/or H2R mediates excitation and long-term potentiation of excitation. In contrast, the H3R autoreceptors provide feedback control of histamine synthesis, release, and electrical activity. As heteroreceptors histamine receptors also function to control exocytosis of several other neurotransmitter systems (e.g., GABA, dopamine, serotonin, etc.). Histamine is also known to play a role in several homoeostatic and/or higher integrative brain functions (such as novelty-induced attention (as opposed to voluntary attention) and adaptation to changing environments). While some overlap between function exists, the activity of the receptors can generally be summarized as in Table 1.

In several embodiments, histamine is provided in a multi-variable approach, in which concentration, volume, and timing can be varied. Other variables can also be changed (such as infusion time, form of histamine, pH, etc.). In several embodiments, a multi-variable pharmacokinetic approach results in selective or enhanced activation of certain receptors. The affinities provided below are used in several embodiments to induce specific and controlled histamine receptor activation, which may in turn reduce or prevent many of the side-effects associated with programs that do not employ the approaches described herein. These side-effects, which may result in non-compliance in taking the therapy, can be avoided or reduced in many embodiments.

mus, thalamus, amygdala, septum, hippocampus and cortex. The H1R signals through one or more of, increased calcium signaling, cyclic guanosine monophosphate (cGMP) mediated signaling, nuclear factor KB (NF-κB), increased phospholipase C (PLC) activity, increased phospholipase A2 and/or D activity, cyclic adenosine monophosphate activity

TABLE 1

Characteristics of Histamine Receptors

| Receptor | Function | Expression | G-protein Subunits | Affinity for Histamine |
|---|---|---|---|---|
| H1 | Smooth muscle contraction (most muscle other than vascular smooth muscle); vasodilation; increases in vascular permeability | Neurons, smooth muscle (e.g., airways, vascular), epithelial, endothelial cells, neutrophils, eosinophils, monocytes, dendritic cells, T-cells, B cells, hepatocytes, and chondrocytes | Gαq/11 | ~1.1 µg/mL |
| H2 | Leukocyte function, gastric parietal cell function (e.g., acid secretion), cardiac stimulation | Gastric mucosa parietal cells, smooth-muscle, heart, epithelial, endothelial cells, neutrophils, eosinophils, monocytes, dendritic cells, T-cells, B cells, hepatocytes, and chondrocytes | Gαs | ~3.33 µg/mL |
| H3 | Central Nervous System neurotransmission; neurotransmission at histaminergic peripheral nerve terminals | Histaminergic neurons, with relatively low expression elsewhere | Gi/o | ~1.1 ng/mL |
| H4 | Hematopoietic and immunocompetent cell function | Bone marrow and peripheral hematopoietic cells, relatively low expression elsewhere | Gi/o | ~2.2-4.4 ng/mL |

Histamine H1 Receptor

Figure 3:
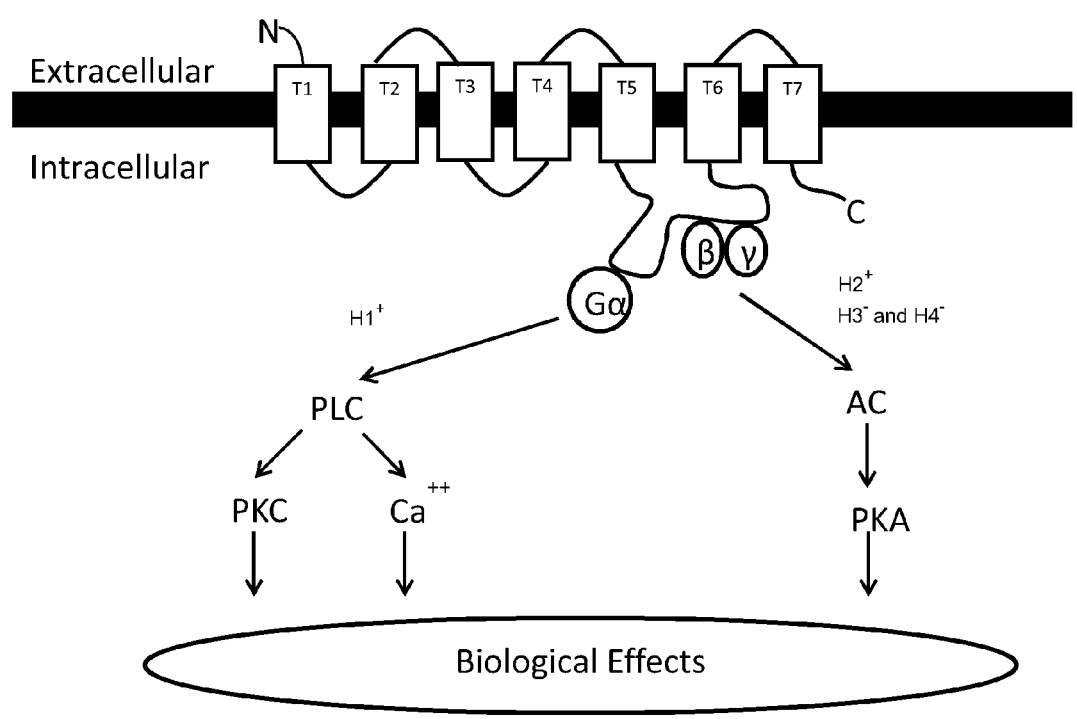
FIG. 3 depicts general schematic of histamine signaling through a G-protein coupled receptor.

The distribution and occupancy of the histamine H1 receptor (H1R) in humans has been mapped using functional imaging techniques to study the sedative properties and blood-brain barrier (BBB) permeability of various H1R antihistamines. Similar studies have been performed in the context of aging and neuropsychiatric disorders, such as Alzheimer's disease, schizophrenia and depression. In most of these studies, H1R binding was found to be lower than in the age matched healthy controls, indicating that histamine imbalance, in several embodiments may be caused, at least in part by elevated H1 receptor expression. Of note is that H1R stimulation has a feed-forward effect on H1R expression (e.g., stimulation of the receptor induces up-regulation in receptor expression). Histamine-induced up-regulation of H1 receptor expression is thought to be mediated by protein kinase C-δ signaling. Mapping studies have also identified a correlation between appearance of various disease symptoms and detection of increased histamine H1 receptor mRNA, as well as a strong correlation between H1R and allergic responses (or responses to antihistamines used to treat allergy). For example, drugs for treatment of allergic symptoms (e.g., antihistamines) not only reduce IL-4 and/or Il-5 expression but also H1 receptor gene expression. Histamine activation of the H1R leads to the release of the several neurotransmitters (e.g., serotonin, dopamine and norepinephrine) and excitation of neurons in most brain regions, including, but not limited to, brain stem, hypothala- (cAMP) and/or nitric oxide synthase activity, and thus can set in motion an enormous variety of signaling cascades associated with these pathways, such as, for example, as cell proliferation, cell differentiation, apoptosis, cytoskeleton remodeling, vesicular trafficking, ion channel conductance, endocrine function and neurotransmission. See FIG. 3 for a schematic representation of histamine receptor signaling.

Histamine H2 Receptor

The activation of H2R regulates various functions of histamine including heart contraction, gastric acid secretion, cell proliferation, differentiation and immune response. In the brain, the highest densities of H2R are found in the basal ganglia, hippocampus, amygdale and cerebral cortex, with lower expression in cerebellum and hypothalamus. H2R stimulates accumulation of cAMP in a variety of tissue including gastric cells, cardiac tissue and brain. In contrast to H1R, activation of H2R is mostly involved in suppressive activities of histamine. For example, it has been demonstrated that H2R activity can inhibit a variety of functions within the immune system and that H2R activity negatively regulates release of histamine in basophils and mast cell. H2R-based inhibition of antibody synthesis, T-cell proliferation, cell mediated cytolysis, and cytokine production is further evidence of H2R presence on lymphocytes, and its negative (e.g., suppressive) effects on histamine.

Histamine H3 Receptor

As indicated above, H3 receptors are primarily expressed in the central nervous system, particularly on histaminergic neurons. H3 receptors couple to Gi/o subunits to inhibit the function of adenylate cyclase and therefore inhibition of cAMP formation, along with accumulation of calcium and stimulation of mitogen-activated protein kinase (MAPK) pathways. H3Rs also mediate synthesis of histamine and their activation leads to inhibition of histamine release from histaminergic neurons. Thus, in several embodiments, preferential stimulation of H3R can counteract activity of the H1R (and thus reducing the feed-forward increase in H1R expression), thereby facilitating restoration of histamine balance. Conversely, H3 receptor blockers may enhance the release of neurotransmitters. Also, activation of H3 receptors leads to inhibitory effects on many neuronal synapses that are non-histaminergic, including, but not limited to those signaling through glutamate, acetylcholine, dopamine, noradrenaline, serotonin, GABA and various peptides.

Histaminergic dysregulation has been found in a variety of different CNS disorders and, as such, various H3 ligands have been investigated for clinical utility in CNS disorders, such as obesity, memory disorders, learning deficit and epilepsy. Additionally, loss of H3R function has been associated with behavioral abnormalities, reduced locomotion, a metabolic syndrome with hyperphagia, late-onset obesity, increased insulin and leptin levels and an increased severity of neuroinflammatory diseases. In several embodiments, the pharmacological properties of the H3R are advantageously exploited in the methods disclosed herein to restore histamine balance/function.

Histamine H4 Receptor

The H4 receptor is involved in cellular mechanisms related to immune systems, inflammatory processes, and allergic reactions. As discussed above, H4 receptors are expressed in bone marrow, spleen, peripheral blood, small intestine, heart, colon, lung, as well as hematopoietic cells, neutrophils, mast cells, eosinophils, basophils, monocytes, T cells and dendritic cells. The H4R mediates eosinophil shape change and mast cell chemotaxis as a result of the βγ subunits acting on phospholipase C, which leads to calcium release, subsequent actin polymerisation and eventually chemotaxis of the mast cells to a site of inflammation.

Histamine Imbalance and Methods of Histamine Receptor Modulation

Normal serum histamine levels (e.g., levels in otherwise healthy subjects without an allergic event) range from about 40 to about 55 ng/mL. Thus, in several embodiments, the rebalancing of the histamine system normalizes the serum histamine level to 40 to about 55 ng/mL. In other embodiments, the rebalancing of the histamine system normalizes the serum histamine level by decreasing or increasing histamine levels by about 30%-70% with respect to baseline. As an example, and as further discussed below, normalizing histamine for a migraine sufferer may be reducing histamine from 120 ng/mL to 70 ng/mL. As discussed above, a condition of low histamine is referred to as histapenia, and a person having low histamine levels is referred to as "histapenic." A condition of high histamine is known as histadelia, and a person having high histamine levels is referred to as histadelic.

Indications for Histamine Therapy

Figure 4:
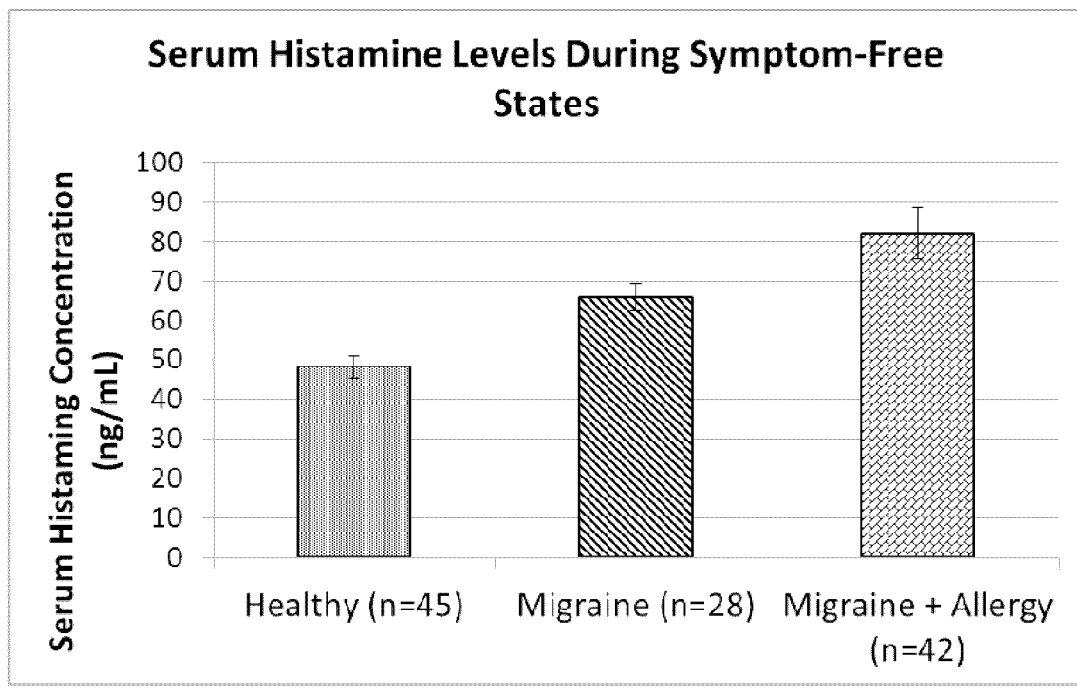
FIG. 4 depicts a summary of previous clinical data related to serum histamine concentrations in various populations during symptom free states.
Figure 5:
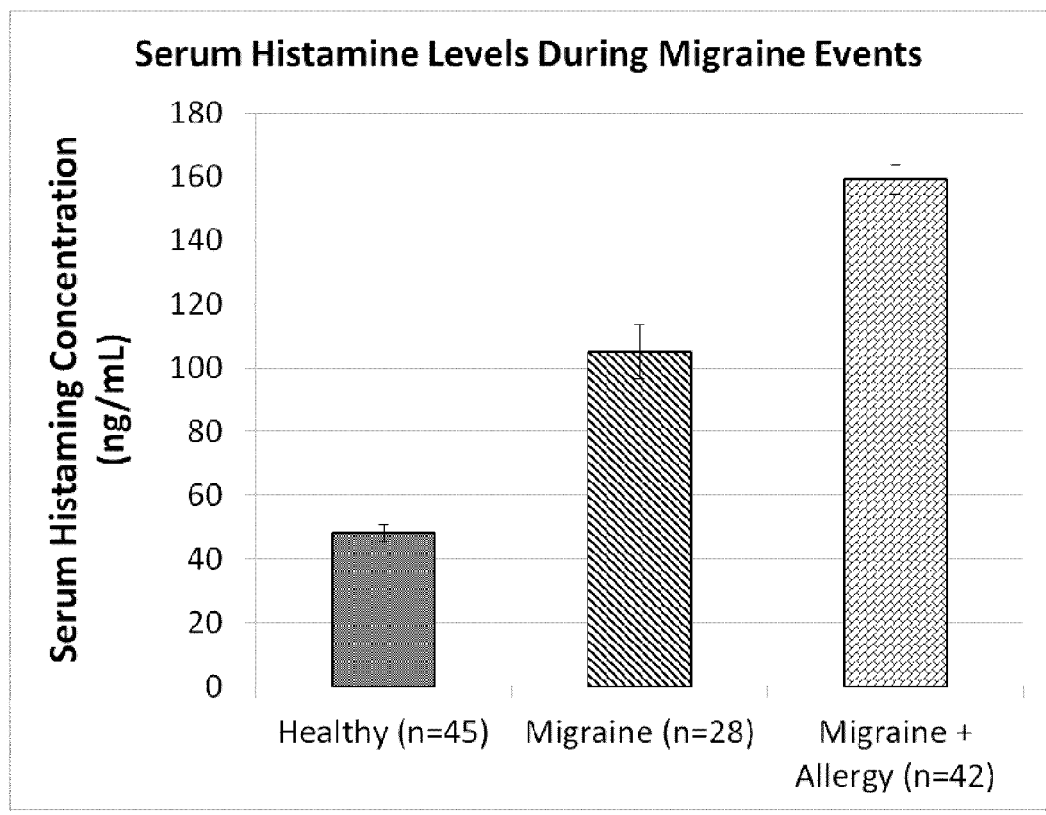
FIG. 5 depicts a summary of previous clinical data related to serum histamine concentrations in various populations during migraine events.

Various ailments and/or illnesses may be caused by, exacerbated by, or linked with an imbalance in the levels of histamine and/or the functionality of the various histamine receptors. As discussed above, normal serum histamine levels range from about 40 to about 55 ng/mL. Histamine levels are imbalanced (e.g., higher or lower than normal) in subjects with ailments or diseases including, but not limited to migraine headaches, vascular headaches, Alzheimer's disease, Parkinson's disease, coronary disease, leukemia, epilepsy, obesity, schizophrenia, Attention-Deficit Hyperactivity Disorders, Huntington's disease, allergies, asthma, autism, Lou Gehrig's disease, atherosclerosis, dementia, addiction and compulsion, metabolic syndrome, rheumatoid arthritis, sleep disorders, alcoholism, substance abuse, cancer, malaria, HIV/AIDS, Central Nervous System (CNS) dysfunctions (e.g., stress, anxiety, depression, movement disorders, anxiety/fear-related disorders, hyperalgesia and brain ischemia), pre-diabetes, diabetes, lupus, cardiac arrhythmias. For example, serum histamine levels in migraine sufferers (who do not also suffer from allergies) during a pain free period can range from about 60 to about 74 ng/mL. Thus, the "normal" histamine levels for a migraine sufferer are elevated as compared to non-migraine sufferers. Thus, migraine sufferers may be inclined to have a migraine episode because of this histamine imbalance. In migraine sufferers who do also suffer from allergies, the resting (e.g., pain free) serum concentrations can range from about 70 to about 95 ng/mL, indicative of a further histamine imbalance (see FIG. 4). These histamine levels are further increased during actual migraine events (see FIG. 5). As with many physiologic parameters, there may be individual-to-individual variability in the concentrations of histamine, however, an imbalance as compared a specific individual's "normal histamine" concentrations (as measured, for example, by serum and/or urine concentrations) can lead to and/or exacerbate various ailments and/or illnesses. Thus, in several embodiments, a histamine receptor activator(s) is provided for use in the treatment of diseases (and/or symptoms) that include but are not limited to migraine headaches, Parkinson's Disease (FIG. 6), Alzheimer's Disease (FIG. 7), coronary disease (FIG. 8), leukemia (FIG. 9), amyotrophic lateral sclerosis and/or epilepsy. Also provided herein are histamine receptor activator (or activators) for use in the treatment of migraine headaches, Parkinson's Disease (FIG. 6), Alzheimer's Disease (FIG. 7), coronary disease (FIG. 8), leukemia (FIG. 9), amyotrophic lateral sclerosis, epilepsy, histadelia and/or histapenia (or other ailments) in patients showing an elevated amount of circulating histamine as well as ailments in which patients show a reduced amount of circulating histamine. Thus, in several embodiments, the invention comprises a histamine receptor activator for use in the treatment of migraine headaches, Parkinson's Disease, Alzheimer's Disease, coronary disease, leukemia, amyotrophic lateral sclerosis, epilepsy, histadelia and/or histapenia and is associated with restoration of histamine balance in the subject. In several embodiments, the invention comprises histamine receptor activator for use in the treatment of diseases associated with the over-expression and/or over-activity of the histamine H1 receptor, or a histamine receptor activator for use in the treatment of diseases associated with the under-expression and/or under-activity one or more of the histamine H2, H3, and/or H4 receptors.

Histamine Therapy for Migraine Headache

Although embodiments disclosed herein are non-limiting and are applicable to several neurological and other conditions, many embodiments are especially useful for migraines. As discussed above, histamine imbalance is common in migraine headache sufferers. Migraine headaches affect more than 30 million people in the United States alone. Roughly 25% of women and 9% of men experience migraine headaches which results in an average of 4 to 6 working days lost each year. In total, this results in an annual loss (nationwide) of between about 64 to 150 million workdays, in turn, equating to direct and indirect costs of nearly $50 billion in the United States alone (according to The National Headache Foundation; see also, J D Bartleson, Treatment of Migraine Headaches, Mayo Clin. Proc. 1999; 74; 702-708). Headache and associated symptoms are responsible for approximately 2% of all visits to emergency departments. Migraine headaches are generally described as recurring, unilateral headache with untreated symptoms lasting from 4 to 72 hours. The international headache Society Classification of headaches lists the presence of at least two of the following symptoms for a headache to be considered a migraine headache: unilateral location, throbbing character, worsening pain with routine activity, and moderate to severe intensity coupled with at least one of the following features: nausea and/or vomiting and photophobia and phonophobia.

At present, there is no known cure for migraine headaches. Migraine treatments are broadly classified as non-pharmacologic or pharmacologic treatments. While several embodiments disclosed herein are related to pharmacologic methods (e.g., administration of a therapeutic agent, such as histamine) to restore histamine balance and treat migraine headaches, in some embodiments, non-pharmacologic and/or combinations of pharmacologic and non-pharmacologic methods are used.

Non-pharmacologic treatments typically involve targeting and/or avoidance of actions and behaviors known to trigger migraine headaches. For example, the non-pharmacologic treatments may include, in several embodiments, regular sleep patterns, routine exercise, avoidance of known triggers. Depending on the individual migraine sufferer, triggers can vary. Food triggers, depending on the embodiment include, but are not limited to ripened cheeses (e.g., cheddar, Emmentaler, Stilton, Brie, and Camembert), chocolate, marinated, pickled, or fermented food, foods that contain nitrites or nitrates (e.g., bacon, hot dogs, deli meats) or MSG (e.g., soy sauce, meat tenderizers, seasoned salt), sour cream, nuts, peanut butter, sourdough bread, various legumes (e.g., broad beans, lima beans, fava beans, snow peas), figs, raisins, papayas, avocados, red plums, citrus fruits, caffeinated beverages such as tea, coffee, or cola, and/or alcoholic beverages. For women, the menstrual cycle may be a trigger, perhaps related to changes in estrogen levels. Light intensity, light patterns (e.g., flickering lights) can also serve as triggers. Stress (e.g., anxiety, worry, shock, sadness, etc.) can also be triggers, as it may set into motion signaling cascades that induce histamine imbalance. Strong odors (e.g., perfumes, chemical odors, odors of certain cooked foods etc.) can also be triggers. In several embodiments, triggers may change over time (e.g., a strong odor may be a trigger in once instance, but not in another). In several embodiments, non-pharmacologic therapies also include, for example, relaxation training, biofeedback training, cognitive and/or behavioral therapy, hypnosis, transcutaneous electrical nerve stimulation, cervical manipulation, and/or hyperbaric oxygen treatments. In several embodiments, the therapeutic agent dosing regimens (e.g., histamine) are supplemented with one or more non-pharmacologic treatments.

Pharmacologic treatments for migraine headaches can generally be divided into two main classes, namely abortive therapies and prophylactic therapies. As used herein, the term "abortive therapies" shall be given its ordinary meaning and shall also refer to therapies that are act to reduce and/or ameliorate symptoms of a migraine that already exists. In several embodiments, the abortive therapies can be further subcategorized into non-specific therapies and migraine specific therapies. In several embodiments, the therapeutic agent dosing regimens (e.g., histamine) are supplemented with one or more pharmacologic treatments. Non-specific therapies that are optionally used in several embodiments include, but are not limited to, for example, analgesics/NSAIDS (e.g., acetaminophen, aspirin, ibuprofen, naproxen sodium, ketorolac), and narcotic analgesics (e.g., meperidine and butorphanol), and adjunctive therapy (e.g., metoclopramide, prochlorperazine). Migraine specific abortive therapies that are optionally used in several embodiments include, but are not limited to ergotamine and/or ergotamine derivatives (e.g., ergotamine, caffeine plus ergotamine, dihydroergotamine) and the members of the tryptamine-based Triptans family (e.g., sumatriptan, naratriptan, rizatriptan, and zolmitriptan). Antihistamines are also used, in several embodiments to preferentially and/or specifically target the activity of certain histamine receptors.

The term "prophylactic therapy" as used herein, shall be given its ordinary meaning and shall include therapies that prevent, avoid, limit and/or otherwise reduce the frequency and/or intensity of migraine headaches. Prophylactic therapies are generally divided into the first-line agents and second-line agents. In several embodiments, first-line therapies for migraine prophylaxis in adults include propranolol, timolol, amitriptyline, divalproex, sodium valproate, and/or topiramate. In several embodiments, second-line agents include one or more of gabapentin, naproxen or naproxen sodium, timed-release dihydroergotamine mesylate, candesartan, lisinopril, atenolol, metoprolol, nadolol, fluoxetine, verapamil, magnesium, vitamin B2 (riboflavin), coenzyme Q10, hormone therapy (e.g., estradiol topical gel), and botulinum toxin type A (Botox).

Many patients continue to experience migraine headaches despite optimal therapy with the currently available therapies. However, in several embodiments, restoration of histamine balance, as disclosed herein, and either alone or in some embodiments, in combination with non-pharmacologic and/or pharmacologic treatments, migraine sufferers can reduce, limit, prevent and/or lessen the frequency and/or intensity of migraine headaches.

In several embodiments, a therapeutic agent (e.g., histamine agonists or antagonists, naturally-occurring or synthetic) is administered to a subject who is a migraine sufferer, in order to establish circulating concentrations of the agent that result, in several embodiments, in suppression of the pro-migraine effects of histamine. In several embodiments, the administration of the therapeutic agents (e.g., histamine, or a synthetic histamine, or an agonist and/or antagonist) result in the concentration of selective interaction of the agents with H3R and/or H2R. As discussed above, activation of the H3R and/or H2R can reduce the synthesis and/or release of histamine, which in turn can reduce the expression of the H1R (due its activity induced increase in expression), and thereby reduce the potential dominance of the H1R and restore balance among the histamine receptors. The various histamine receptors are thus specifically targeted by a histamine receptor activator(s) for use in the treatment of migraine headaches, Parkinson's Disease, Alzheimer's Disease, coronary disease, leukemia, amyotrophic lateral sclerosis, epilepsy, histadelia and/or histapenia, and other disorders.

Previous studies have been directed towards histamine administration regimens. For example, during a controlled, double-blinded, clinical trial for migraine prevention, histamine was administered, twice a week and for 12 weeks, in consecutively increasing subcutaneous doses (0.1 to 1 ng) to compare efficacy of histamine versus to placebo for prophylaxis of migraine. See Guerrero R O, et al., Histamine as a therapeutic alternative in migraine prophylaxis: a randomized, placebo-controlled, double-blind study, Headache, Vol. 39(8): 576-80 (1999).

In another study, $N^\alpha$-methylhistamine was administered at doses of 1 to 3 ng twice a week, which significantly reduced (P<0.0001) the frequency, intensity, and duration of migraine attacks, as well as the need for rescue analgesics. However, at doses greater than 3 ng, patients experienced adverse side effects manifest as intense headache. See Millan-Guerrero R O, et al., $N^\alpha$-Methylhistamine Safety and Efficacy in Migraine Prophylaxis: Phase I and Phase II Studies, Headache Vol. 43:389-394 (2003) and Millan-Guerrero R O, et al., N$\alpha$-Methyl Histamine Safety and Efficacy in Migraine Prophylaxis: Phase III Study Can. J. Neurol. Sci., Vol. 33: 195-199 (2006).

In another comparative study, subcutaneous histamine (10 μg/mL in Evan's solution) was administered twice weekly, with an initial administration of 1 μg (0.1 mL) and gradually increasing dose to 10 μg (1.0 mL) over a 12-week period. Histamine was compared to placebo, sodium valproate, and topiramate administration. The histamine group reported a reduction of headache frequency (50%), decrease in pain intensity (51%), length of migraine attacks (45%) and painkiller use (52%). See Millán-Guerreroa R O, et al., Nueva alternativa terapéutica en profilaxis de migraña con histamina como agonista de receptores H3 Gac Méd Méx Vol. 144 No. 4: 291-295 (2008).

Histamine was also compared to sodium valproate in a 12-week double-blind controlled clinical trial. Subcutaneous administration of histamine (1-10 ng twice a week) was compared with oral administration of sodium valproate (500 mg daily dose). Data collected during the 4th, 8th and 12th weeks of treatment revealed that histamine caused a significantly greater reduction (P<0.001) in intensity and duration of migraine attacks as well as in analgesic intake. No difference was detected in the frequency of attacks or in MIDAS. See Milian-Guerreroa R O, et al., Subcutaneous histamine versus sodium valproate randomized, controlled, double-blind study European Journal of Neurology, Vol. 14: 1079-1084 (2007). A similar trial compared subcutaneous administration of histamine (1-10 ng twice a week) with oral administration of topiramate (100 mg daily dose). See Millan-Guerreroa R O, et al., Subcutaneous Histamine versus Topiramate in Migraine Prophylaxis: A Double-Blind Study, Eur Neurol; Vol. 59:237-242 (2008). An additional trial compared histamine (subcutaneous, 1-10 ng, twice per week) with Botox injection (50 Units, one injection cycle). See Millan-Guerrero R O, et al., Subcutaneous histamine versus botulinum toxin type A in migraine prophylaxis: a randomized, double-blind study, European Journal of Neurology, Vol. 16: 88-94 (2009).

Additional studies have shown that in migraine subjects, intravenous administration of relatively high doses of histamine (e.g., 0.5 mg/kg per minute for 20 min) caused an immediate headache during the infusion, followed by a delayed migraine attack. Those side effects could abolished by pre-treatment with the H1R antagonist mepyramine. See Krabbe and Olesen (Krabbe A A, 1980) and Lassen et al. (Lassen L H, 1995).

Other studies report methods of determining histamine dosing regimens. One such approach is empiric optimum dosing while another is objective endpoint titration. Empiric optimum dosing involves injection of histamine with a particular frequency (e.g.,) once or twice a week to initiate treatment in conjunction with supplementation by daily sublingual drops. The dose of histamine is increased to the point of optimum clinical response, but short of aggravation. An objective endpoint titration approach involves determining the dose of histamine that induces an allergic response (e.g., successively more concentrated intracutaneous doses are administered until an allergic wheal results). That dose is defined as the treatment dose, and subcutaneous injections of that dose are administered at a declining frequency.

In spite of ongoing histamine research and uses of histamine in various therapeutic contexts, there remains a need for histamine dosing regimens that are capable of restoring the body's natural histamine function, and that can treat disease states caused by imbalances in the body's release and metabolism of histamine, such as, for example, migraine headache. Additionally, therapeutic benefit may not be realized by subjects who are treated with therapies in accordance to the studies discussed above, and/or such therapeutic benefit may be associated with side effects. Moreover, in contrast to the methods disclosed herein, many current attempted therapeutic uses of histamine do not account for the selective activation of specific histamine receptors (several embodiments of the disclosed methods are based on the exploitation of the differing pharmacological characteristics of the histamine receptors), which unexpectedly provides exceptional therapeutic results and treatments for histapenia, histadelia, and/or disorders that are related to or associated with histamine imbalance.

Thus, several embodiments of the invention provide an escalating dosing regimen comprising in sequential order (a) a first dosing segment comprising two or more sequential doses of a therapeutic agent (e.g., histamine, or a salt thereof, such as, for example, histamine phosphate or histamine dihydrochloride) separated by one or more equal time intervals (the "first time interval"), wherein the concentration of the agent is increased from dose to dose while the administered volume of each dose stays constant; and (b) a second dosing segment comprising two or more sequential doses of the therapeutic agent separated by one or more equal time intervals (the "second time interval"), wherein the concentration of the agent increases from dose to dose while the administered volume of each dose stays constant; wherein the volume of each dose in the second dosing segment is greater than the volume of each dose in the first dosing segment, and the second time interval is longer than the first time interval.

As used herein, the terms "first" and "second" are used in relation to one another, and not to the overall dosing regimen. Thus, the dosing regimen can comprise more than two dosing segments, in which case the first dosing segment can refer to any dosing segment within the dosing regimen other than the last dosing segment, and the second dosing segment can refer to any dosing segment performed after the first dosing segment. Depending on the embodiment, the regimen may comprise 2, 3, 4, 5, 6, 7, 8, 9, 10 or more total dosing segments. Thus, the first dosing segments can be any of segments 1 through 9, while the second dosing segment can be any succeeding dosing segment 2 through 10.

In several embodiments, the dosing regimen is a fixed regimen, in that the complete regimen is administered to the patient in order to achieve optimal therapeutic benefits (e.g., if the regimen is 10 segments, then all 10 segments are completed). However, in several embodiments, the regimen is optionally truncated for one or more of a variety of reasons. In several embodiments, the regimen is truncated because the patient received the regimen has experienced a sufficient therapeutic benefit. For example, in several embodiments directed to migraine treatment, the subject may have experienced a significant reduction in pain, frequency, duration, and/or intensity of migraine episodes. In several embodiments, the subject can restart a regimen after a given period of time, for example several days to several months, including about 2 to about 7 days, about 7 to about 14 days, about 14 to about 21 days, about 21 days to about 4 weeks, about 4 weeks to about 8 weeks, about 8 weeks to about 12 weeks, and overlapping ranges thereof. A subject may restart a regimen at the point that the regimen was optionally truncated (e.g., picking up where the subject left off). The regimen may also be restarted from the point of inception (e.g., dose #1 of segment #1). Restarting the regimen may be due to a reduction in the benefits from the prior administration of the regimen (e.g., return of symptoms and/or increase in, for example, migraine frequency). While several embodiments of the methods disclosed herein are surprisingly without side effects (e.g., in some segments, the doses of histamine exceed those that have caused side effects in other studies, but do not induce side effects such as migraines), in several embodiments, the regimen is optionally truncated due to side effects. Depending on the clinical conditions, the regimen can be cut short either by stopping at a particular dosing volume within a dosing segment, or by stopping before performing a succeeding segment. In several embodiments, rather than a truncation, a subject can maintain a particular segment of the regimen for one or more time periods (e.g., repeat segment #4 for a plurality of time intervals), or repeat a previously administered segment one or more times (e.g., rather than administer segment #4, re-administer segment #3 for one or more time periods).

In several embodiments, the number of doses administered during the first dosing segment is equal to the number of doses administered during the second dosing segment. In several embodiments, one or all of the segments can comprise 2, 3, 4, 5, 6, 7, 8 or more doses. In several embodiments, four individual doses are given in the first dosing segment. In several embodiments, subsequent dosing segments have four individual doses. In some embodiments, the number of doses is greater or lesser, depending on the needs and clinical symptoms of a given patient. For example, in several embodiments 2-3, 3-4, 4-8, 8-12, or 12-24 (and overlapping ranges thereof) doses are administered within a given dosing segment. Each dosing segment can comprise a different number of doses although, as noted above, in several embodiments, each segment preferably includes the same number of doses.

Additionally, in several embodiments, the first dosing segment and the second dosing segment are separated by a first time interval. In several embodiments, the time interval ranges from about 3 to about 30 days, including about 3 to about 5, about 5 to about 7, about 7 to about 10, about 10 to about 15, about 15 to about 20, about 20 to about 25, about 25 to about 30 days, and overlapping ranges thereof. As discussed herein, in certain embodiments, the time interval varies between, for example the first and second segments, as compared to, for example, the fourth and fifth segments. In several embodiments, the time interval is determined by a subject's responsiveness (or refractoriness) to a dosing segment. In additional embodiments, the dosing segment interval is determined by other variables, such as for example, convenience or personal preference of the subject. In several embodiments, the first dosing segment is optionally administered on a compressed time-frame. For example, in several embodiments the doses comprising the first therapy segment are, in several embodiments, administered within a shortened time frame 1-2 minutes, about 2-3 minutes, about 3-4 minutes, about 4-5 minutes, about 5-10 minutes, about 10-20 minutes, about 20-30 minutes, and overlapping ranges thereof. In several embodiments, the first therapy segment comprises simultaneously delivery of each of the doses within the segment. As a result, the modulation of the various receptors occurs on a reduced time-frame, and in some embodiments, simultaneously.

In several embodiments, the dosing regimen further comprises at least a third dosing segment comprising two or more sequential doses of the therapeutic agent (e.g., histamine) separated by one or more equal time intervals (the "third time interval"). In several embodiments, the concentration of the agent increases from dose to dose while the administered volume of each dose within the segment stays constant, and the volume of each dose in the third dosing segment is greater than the volume of each dose administered in the second dosing segment. Further, in several embodiments the third time interval is longer than the second time interval (though, in some embodiments, the time interval can optionally be altered to be equivalent to, or shorter than, the time interval of a preceding dosing segment). This third dosing segment can be any segment that follows the second segment in a multiple segment regimen.

In several embodiments comprising at least three administration segments, (i) the concentrations of the therapeutic agent (e.g., histamine, such as histamine phosphate or histamine dihydrochloride) administered during the third dosing segment are the same as the concentrations of the therapeutic agent (e.g., histamine, such as histamine phosphate or histamine dihydrochloride) administered during the second dosing segment; (ii) the number of doses administered during the third dosing segment is equal to the number of doses administered during the second dosing segment; and (iii) the second dosing segment and the third dosing segment are separated by the second time interval.

In some embodiments, the dosing regimen comprises up to 10 sequential dosing segments, wherein (a) each dosing segment comprises two or more sequential doses of the therapeutic agent (e.g., histamine) separated by one or more equal time intervals, (b) concentration of the agent increases from dose to dose while the administered volume of each dose stays constant; (c) the volume of each dose in a succeeding dosing segment is greater than the volume of each dose in the preceding dosing segment; (d) the time interval in each succeeding dosing segment is longer than the time interval in the preceding dosing segment; (e) the concentrations of the agent administered are the same in each dosing segment; (f) the number of doses administered during each segment is equal; and (g) each succeeding dosing segment is separate from the immediately preceding dosing segment by the time interval observed for the immediately preceding dosing segment.

As discussed above, in several embodiments, the individual doses within a segment are given in a constant volume. For example, in several embodiments, the first dosing segment comprises a plurality of individual doses, each administered in a volume of between about 0.01 to about 1.0 mL, including about 0.01 mL to about 0.05 mL, about 0.05 mL to about 0.10 mL, about 0.10 mL to about 0.15 mL, about 0.15 mL to about 0.20 mL, about 0.20 mL to about 0.50 mL, about 0.50 mL to about 0.75 mL, about 0.75 mL to about 1.0 mL, and overlapping volumes therebetween. In several embodiments, the volume of therapeutic agent (e.g., histamine) administered in each subsequent segment is greater than the volume of the therapeutic agent administered in the immediately preceding segment. For example, if the volume of the therapeutic agent administered in a first segment is 0.1 mL, the volume of the therapeutic agent administered in the next segment is greater than 0.1 mL. In several embodiments, the volume of the therapeutic agent administered in a given dosing segment is 0.1 ml greater than the previous segment. In several embodiments, the volume of the therapeutic agent administered in the last segment ranges from about 0.1 to about 10 mL, including about 0.1 mL to about 1.0 mL, about 1.0 mL to about 2.0 mL, about 2.0 mL to about 5.0 mL, about 5.0 mL to about 7.5 mL, about 7.5 mL to about 10.0 mL, and overlapping volumes therebetween. In several embodiments, the volume of the therapeutic agent administered in the last segment is about 1.0 mL.

In several embodiments, the concentration of the therapeutic agent (e.g., histamine) administered within each segment increases with each individual dose. For example, in the first (e.g., the starting) segment, the concentration of the therapeutic agent can range from about 0.1 attogram/mL to about 10 µg/mL, including about 0.1 attogram/mL to about 1 attogram/mL, about 1 attogram/mL to about 1 femtogram/mL, about 1 femtogram/mL to about 1 picogram/mL (pg/mL), about 1 pg/mL to about 100 pg/mL, about 100 pg/mL to about 200 pg/mL, about 200 pg/mL to about 300 pg/mL, about 300 pg/mL to about 400 pg/mL, about 400 pg/mL to about 500 pg/mL, about 500 pg/mL to about 600 pg/mL, about 600 pg/mL to about 700 pg/mL, about 700 pg/mL to about 800 pg/mL, about 800 pg/mL to about 900 pg/mL, about 900 pg/mL to about 1 ng/mL, about 1 ng/mL to about 5 µg/mL, about 0.1 µg/mL to about 3 µg/mL, and overlapping ranges thereof. In several embodiments, the next dose is greater than the immediately preceding dose. In several embodiments, the final dose in a segment ranges from about 0.1 µg/mL to about 20 µg/mL, including from about 1 µg/mL to about 2 µg/mL, about 2 µg/mL to about 3 µg/mL, about 3 µg/mL to about 3.5 µg/mL, about 3.5 µg/mL to about 4 µg/mL, about 4 µg/mL to about 6 µg/mL, about 6 µg/mL to about 8 µg/mL, about 8 µg/mL to about 10 µg/mL, and overlapping ranges thereof. Thus, the concentrations from the initial dose within a segment to the final dose within a segment range from about 0.1 attogram/mL to about 20 µg/mL, from about 1 pg/mL to about 1 ng/mL, from about 1 ng/mL to about 1 µg/mL, from about 1 µg/mL to about 3.5 µg/mL, from about 3.5 µg/mL to about 15 µg/mL, from about 15 µg/mL to about 20 µg/mL, and overlapping ranges thereof. In some embodiments, the ratio of total amounts given in each therapy segment is 1:2:3 (for three segments), 1:2:3:4 (for four segments), 1:2:3:4:5 (for five segments). In some embodiments, the ratio of individual doses within in a given therapy segment is $1:10^3:10^6:3.5\times10^6$. The concentrations of the therapeutic agents (e.g., histamine) provided herein can be the dose administered to the subject, or in certain embodiments, the plasma concentration achieved.

In several embodiments, the overall dose for a segment (e.g., the total quantity of a therapeutic agent, such as histamine, administered in each dose within a segment) preferably falls with the following ranges:

Segment 1
  Initial Dose: about 0.1 attogram to about 1 ng, or about 100 attograms to about 10 pg
  Concluding Dose: about 1 ng to about 1 µg, or about 100 ng to about 500 ng
Segment 2
  Initial Dose: about 1000 attograms to about 1 ng, or about 0.1 pg to about 100 pg
  Concluding Dose: about 10 ng to about 10 µg, or about 1 µg to about 5 µg More specifically, in several embodiments, each individual dose within a segment is designed to target a specific histamine receptor (or receptors), based on the affinity of the various receptors for histamine (see e.g. Table 1). For example, an initial dosing segment that comprises four doses, D1, D2, D3, and D4, with D1 being the lowest concentration and D4 being the highest concentration would target, respectively H3/H4, H3/H4, H1, and H2. Further, as a non-limiting example, in embodiments in which histamine is administered, the total amount of histamine administered in D1 ranges from about from about 0.0001 pg to about 999 pg, the total amount of histamine administered in D2 ranges from about from about 1 ng to about 999 ng, the total amount of histamine administered in D3 ranges from about from about 1 µg to about 3.499 µg (for example about 1 µg to about 2.999 µg), and the total amount of histamine administered in D4 ranges from about from about 3.0 µg to about 10 µg (for example about 3.5 µg to about 10 µg). As discussed above, and continuing the non-limiting example, a second dosing segment comprising 4 doses, D5, D6, D7, and D8, which, in several embodiments, are of a greater volume than the doses in the first dosing segment, results in administration of greater amounts of histamine (not only with respect to the corresponding dose in the previous segment, but also with respect to the immediately preceding dose within the current segment, if any). Thus, for example, the total amount of histamine administered in D5 ranges from about from about 0.0002 pg to about 1998 pg, the total amount of histamine administered in D6 ranges from about from about 2 ng to about 1998 ng, the total amount of histamine administered in D7 ranges from about from about 2 µg to about 5.998 µg (for example about 2 µg to about 5.998 µg), and the total amount of histamine administered in D8 ranges from about from about 7.0 µg to about 20 µg. In some embodiments, the ratio of total amounts given in each therapy segment is 1:2:3 (for three segments), 1:2:3:4 (for four segments), 1:2:3:4:5 (for five segments). In some embodiments, the ratio of individual doses within in a given therapy segment is $1:10^3:10^6:3.5\times10^6$.

As a further example of the targeting of a specific histamine receptor (or receptors) based on dose, timing of administration, concentration, etc. the concept of natural/resonant frequencies may be informative. A given object possesses a natural frequency at which it will vibrate upon excitation. For example, a guitar string tuned to a specific pitch and plucked with a given force will vibrate at a natural frequency. A different string tuned to a different pitch will vibrate at its own natural frequency. The measure of natural frequency depends on the composition of a particular object, its size, structure, weight and shape. If a vibrating force is applied to an object with the frequency of the vibrating force equal to the natural frequency, a resonance condition results. The histamine receptors can conceptually be analogized to objects with differing resonant frequencies. For example, if the H1 receptor has a resonant frequency of X, the H2 receptor has a resonant frequency of Y, the H3 receptor has a resonant frequency of Z, and the H4 receptor has a resonant frequency of A, application of a vibration force (e.g., a histamine concentration) at X, Y, Z, or A will result in specific stimulation of one of the histamine receptor types. As a further example, consider three blocks (one for H1 receptors, one for H2 receptors, and one for H3 receptors), each with a different natural frequency. Application of a vibration force (e.g., a histamine concentration) at or near the natural frequency of the block (e.g., the concentration at which histamine activates the specific receptor type) will cause resonant frequency movement of that block (e.g., receptor activation) while the other blocks, although perhaps moving, are not at their resonant frequencies (e.g., the receptors may have some activation, but less than that of the peak activation resulting from certain concentrations of histamine). Further, when a vibration force greater than the natural frequency of a block is applied, the block may no longer respond or may respond to a lesser degree. However, an additional block, that didn't respond to the first force, may respond to the second force, if it approaches the natural frequency of the block. See also, for example the video at http://www.youtube.com/watch?v=LV_UuzEznHs (by Professor O. Kwan, Department of Civil Engineering, University of Toronto; video incorporated by reference herein). Further in several embodiments, the blocks (e.g., various histamine receptors) may respond at different harmonics, multiples of the resonant frequency (e.g., multiples or fractions of a histamine concentration that causes receptor activation). As discussed in more detail herein, not all histamine concentrations produce the same effect on the histamine receptors (H1R-H4R) and exciting a specific histamine receptor at a given histamine concentration approximating its specific affinity for histamine, forces that specific receptor to "resonate", resulting in increased specific receptor activation.

Depending on the embodiment, the duration of each dosing segment can vary. In several embodiments, the duration of the segment ranges from about one day to about one week, including about 1 to about 2 days, about 2 to about 4 days, about 4 days to about 6 days, about 5 days to about 7 days, and overlapping ranges thereof. In several embodiments, the dosing segments range from about 1 week to about 16 weeks, including about 1 to about 2 weeks, about 2 to about 3 weeks, about 3 to about 4 weeks, about 4 to about 6 weeks, about 6 to about 9 weeks, about 9 to about 12 weeks, about 12 to about 16 weeks, and overlapping ranges thereof. In several embodiments, a subsequent dosing segment is longer in duration that it's immediately preceding dosing segment.

For example, in several embodiments, wherein a first dosing segment is about 2 weeks, a second dosing segment is, for example, about 2 to about 4 weeks in duration. In several embodiments, comprising additional segments, the duration of each segment continues to increase. In several embodiments, a subsequent dosing segment is longer in duration than its immediately preceding dosing segment. Depending on the embodiment (e.g., the duration of the dosing segment and the number of individual doses within a segment), the dosing frequency within a segment can range from daily dosing to dosing once every several weeks. In several embodiments, dosing within a segment occurs daily, every two days, every third day, every fifth day, once per week, twice per week, once every 10 days, once every two weeks, once every three weeks, once every month, once every six weeks, and frequencies within those listed. In several embodiments, as the number of dosing segments increases, a subsequent dosing segment has a reduced dosing frequency as compared to its immediately preceding dosing segment. In several embodiments, a subsequent dosing segment not only longer in duration than its immediately preceding dosing segment, the subsequent dosing segment has a reduced dosing frequency as compared to its immediately preceding dosing segment. Table 2 depicts a non-limiting example of a dosing regimen in accordance with several embodiments disclosed herein. In some embodiments, one or more segment durations are compressed by 50% to 99% (e.g., 60%, 75%, 85%, 90%, 95%). As a non-limiting example, the 4 steps of Segment 1 can be done in a single day.

TABLE 2

Example of Dosing Regimen

| Segment Number | Step Number | Concentration of Therapeutic Agent* | Volume Administered | Segment Duration |
|---|---|---|---|---|
| Segment 1 | 1 | 0.00001-999 pg/mL | 0.01-1.0 mL | 1 day to 2 weeks (e.g., 1 day to 1 week) |
|  | 2 | 1-999 ng/mL | 0.01-1.0 mL | 1 day to 2 weeks (e.g., 1 day to 1 week) |
|  | 3 | 1-3.499 µg/mL | 0.01-1.0 mL | 1 day to 2 weeks (e.g., 1 day to 1 week) |
|  | 4 | 3.5-10 µg/mL | 0.01-1.0 mL | 1 day to 2 weeks (e.g., 1 day to 1 week) |
| Segment 2 | 5 | 0.00001-999 pg/mL | 0.02-2.0 mL | 3 days to 3 weeks (e.g., 3 days to 2 weeks) |
|  | 6 | 1-999 ng/mL | 0.02-2.0 mL | 3 days to 3 weeks (e.g., 3 days to 2 weeks) |
|  | 7 | 1-3.499 µg/mL | 0.02-2.0 mL | 3 days to 3 weeks (e.g., 3 days to 2 weeks) |
|  | 8 | 3.5-10 µg/mL | 0.02-2.0 mL | 3 days to 3 weeks (e.g., 3 days to 2 weeks) |
| Segment 3 | 9 | 0.00001-999 pg/mL | 0.03-3.0 mL | 1 week to 4 weeks (e.g., 1 week to 3 weeks) |
|  | 10 | 1-999 ng/mL | 0.03-3.0 mL | 1 week to 4 weeks (e.g., 1 week to 3 weeks) |
|  | 11 | 1-3.499 µg/mL | 0.03-3.0 mL | 1 week to 4 weeks (e.g., 1 week to 3 weeks) |
|  | 12 | 3.5-10 µg/mL | 0.03-3.0 mL | 1 week to 4 weeks (e.g., 1 week to 3 weeks) |
| Segment 4 | 13 | 0.00001-999 pg/mL | 0.04-4.0 mL | 2 weeks to 5 weeks (e.g., 2 weeks to 4 weeks) |
|  | 14 | 1-999 ng/mL | 0.04-4.0 mL | 2 weeks to 5 weeks (e.g., 2 weeks to 4 weeks) |
|  | 15 | 1-3.499 µg/mL | 0.04-4.0 mL | 2 weeks to 5 weeks (e.g., 2 weeks to 4 weeks) |
|  | 16 | 3.5-10 µg/mL | 0.04-4.0 mL | 2 weeks to 5 weeks (e.g., 2 weeks to 4 weeks) |

TABLE 2-continued

Example of Dosing Regimen

| Segment Number | Step Number | Concentration of Therapeutic Agent* | Volume Administered | Segment Duration |
|---|---|---|---|---|
| Segment 5 | 17 | 0.00001-999 pg/mL | 0.05-5.0 mL | 3 weeks to 6 weeks (e.g., 3 weeks to 5 weeks) |
| | 18 | 1-999 ng/mL | 0.05-5.0 mL | 3 weeks to 6 weeks (e.g., 3 weeks to 5 weeks) |
| | 19 | 1-3.499 µg/mL | 0.05-5.0 mL | 3 weeks to 6 weeks (e.g., 3 weeks to 5 weeks) |
| | 20 | 3.5-10 µg/mL | 0.05-5.0 mL | 3 weeks to 6 weeks (e.g., 3 weeks to 5 weeks) |
| Segment 6 | 21 | 0.00001-999 pg/mL | 0.06-6.0 mL | 4 weeks to 7 weeks |
| | 22 | 1-999 ng/mL | 0.06-6.0 mL | 4 weeks to 7 weeks |
| | 23 | 1-3.499 µg/mL | 0.06-6.0 mL | 4 weeks to 7 weeks |
| | 24 | 3.5-10 µg/mL | 0.06-6.0 mL | 4 weeks to 7 weeks |
| Segment 7 | 25 | 0.00001-999 pg/mL | 0.07-7.0 mL | 5 weeks to 8 weeks |
| | 26 | 1-999 ng/mL | 0.07-7.0 mL | 5 weeks to 8 weeks |
| | 27 | 1-3.499 µg/mL | 0.07-7.0 mL | 5 weeks to 8 weeks |
| | 28 | 3.5-10 µg/mL | 0.07-7.0 mL | 5 weeks to 8 weeks |
| Segment 8 | 29 | 0.00001-999 pg/mL | 0.08-8.0 mL | 6 weeks to 9 weeks |
| | 30 | 1-999 ng/mL | 0.08-8.0 mL | 6 weeks to 9 weeks |
| | 31 | 1-3.499 µg/mL | 0.08-8.0 mL | 6 weeks to 9 weeks |
| | 32 | 3.5-10 µg/mL | 0.08-8.0 mL | 6 weeks to 9 weeks |
| Segment 9 | 33 | 0.00001-999 pg/mL | 0.09-9.0 mL | 7 weeks to 10 weeks |
| | 34 | 1-999 ng/mL | 0.09-9.0 mL | 7 weeks to 10 weeks |
| | 35 | 1-3.499 µg/mL | 0.09-9.0 mL | 7 weeks to 10 weeks |
| | 36 | 3.5-10 µg/mL | 0.09-9.0 mL | 7 weeks to 10 weeks |
| Segment 10 | 37 | 0.00001-999 pg/mL | 1.0-10 mL | 8 weeks to 12 weeks |
| | 38 | 1-999 ng/mL | 1.0-10 mL | 8 weeks to 12 weeks |
| | 39 | 1-3.499 µg/mL | 1.0-10 mL | 8 weeks to 12 weeks |
| | 40 | 3.5-10 µg/mL | 1.0-10 mL | 8 weeks to 12 weeks |

*Table 2: All concentrations represent concentrations of the active principle of the therapeutic agent. For example, in the case of a salt of an agent, the concentrations account for the molecular weight of the salt versus the molecular weight of the agent alone. Additionally, within a segment, the administration of the concentrations to any desired order depending on the embodiment.

In several embodiments, the invention comprises a dosing regimen in which the volume, concentration, and/or timing of administration of a therapeutic agent (e.g., histamine or salt of histamine) is administered variably. Other approaches employ singular variability (e.g., changing only one of concentration, volume, or timing). Advantageously, however, several embodiments of the methods employ such three-dimensional variability and result an unexpectedly more robust therapeutic effect. In several embodiments, the improved therapeutic effect is achieved without significant side effects. In several embodiments, the improved efficacy is derived from the more specific histamine receptor targeting that the varied concentrations for each dose achieve (e.g., the concentrations of the various doses exploit the varied affinity of the H1R-H4R for histamine, or other therapeutic agent). In several embodiments, the increase in volume from segment to segment allows a greater proportion of the histamine receptors in a given area to be activated (or suppressed depending on the particular receptor and/or the amount of histamine given). The varied timing, in several embodiments, helps prevent receptor desensitization that could result if frequency of administration were constant over time. In such a case, an increased dose would be administered at constant intervals, which could result in one or more of the histamine receptors becoming refractory to the histamine, particularly in view of the increased dose from segment to segment. Thus, as a subject proceeds through the segments in a given regimen, the variability in concentration, volume, and timing result in effects on the various histamine receptors (e.g., upregulation or downregulation in activity and/or expression) that result in restoration of histamine balance.

In several embodiments, dosing regimens in accordance with the methods disclosed herein (a non-limiting example of which is shown in Table 2) can be used to return patients histamine concentrations to optimum histamine ranges, whether their histamine levels are above or below the optimum (healthy population) histamine level (plasma or urine). Advantageously, depending on the embodiment, the concentration range presented in each step (for example Segment 1, Step Number 2) allows for multiple "subconcentrations" to be implemented as part of the dosing regimen. For example, as discussed in more detail below, Table 3 shows a non-limiting embodiment where C1=1.1 ng/mL and C2 is 3 ng/mL.

In several embodiments, the methods enable the lowering of histamine levels in a patient having a histamine level above a level required for optimum histamine function (e.g., histadelia), comprising administering histamine (synthetic to natural), a histamine agonist or antagonist, or a pharmaceutically acceptable salt thereof to the patient according to the dosing regimens disclosed herein. In several embodiments, the methods disclosed herein enable the increase of histamine levels in a patient having a histamine level below a level required for optimum histamine function (e.g., histapenia), comprising administered histamine (synthetic to natural), a histamine agonist or antagonist, or a pharmaceutically acceptable salt thereof to the patient according to the dosing regimens disclosed herein.

In several embodiments, there are also provided "combination" dosing regimens that are used to facilitate returning a patient's histamine concentrations to within optimum ranges for that individual (e.g., whether that particular patient's histamine levels are above or below the average of a healthy population. As with several other embodiments disclosed herein, the combination regimen enables the lowering of histamine levels in a patient having a histamine level above a level required for optimum histamine function (e.g., histadelia). The method comprises, in several embodiments, administering histamine (synthetic or natural), a histamine agonist or antagonist, or a pharmaceutically acceptable salt thereof to the patient according to the non-limiting dosing regimen shown in Table 3. In several embodiments, the combination dosing regimen enables the increase of histamine levels in a patient having a histamine level below a level required for optimum histamine function (e.g., histapenia), the method comprising administering histamine (synthetic or natural), a histamine agonist or antagonist, or a pharmaceutically acceptable salt thereof to the patient according to the non-limiting dosing regimen shown in Table 3.

In several embodiments, the combination regimen comprises a plurality (e.g., 2, 3, 4, 5, 6, or more) of initial segments, each comprising, for example, four individual doses (although a greater number of doses may optionally be administered). As discussed in relation to other embodiments disclosed herein, the concentration of each dose is increased with respect to one another, but the volume administered is held constant across a given dosing segment. In additional embodiments, one or more of the concentration or volume may also be varied, based on the individual subject's needs and/or symptoms. In some embodiments, the initial segments serve as a "loading period", in that histamine is initially administered in a reciprocating pattern. For example, segment 1 of Table 3 comprises four doses, each increasing in concentration relative to one another. The first dose of segment 2, however, is lower than the final dose of segment 1. Thus the doses increase over a given segment, then drop back to concentrations that are less than the concentration of the last dose administered. This "two step forward, one step back" approach enables the gradual manipulation of the various histamine receptors and a more gradual re-establishment of histamine levels, which advantageously reduces risk of side effects. After the initial segments have been administered, a "loading dose" of histamine (or agonist/antagonist, etc.) has been established and, advantageously, one or more of the individual doses can be eliminated in subsequent dosing segments. Therefore, in several embodiments, dosing regimens, such as the non-limiting embodiment of the dosing regimen shown in Table 3, can be directed to only a portion of the histamine receptors. For example, the non-limiting embodiment of the dosing regimen shown in Table 3 is directed to the H1, H2, H3 and H4 receptors. In additional embodiments, however, doses and/or volumes are adjusted to enable targeting of, as an example, H1 and/or H2, and/or H3 receptors. Additionally, in some embodiments, dosing regimens target only two histamine receptors. In such embodiments, the volumes and concentrations are adjusted accordingly. For example, the non-limiting example dosing regimen in Table 3 could be adjusted to target H2 and H3 receptors or H2 and H4 receptors.

Additionally, as shown in an additional non-limiting embodiment in Table 3A, after dosing segment 3, each subsequent dosing segment comprises 3 doses, with concentration 1 (C1) having been eliminated from the doses. In several embodiments, concentration 1 is eliminated because both C1 and C2 are directed at the H3 and/or H4 receptors. Thus, multiple doses directed to these two receptors may, in several embodiments, induce a refractoriness to histamine (e.g., the H3 and/or H4 receptor may become less sensitive if over stimulated) or may induce a change in expression (e.g., a reduction or increase in gene, or protein, that would reduce the efficacy of doses targeting H3 and/or H4). Moreover, in several embodiments, the use of a single dose targeting the H3 and/or H4 receptors reduces risks of adverse side effects or sensitivity to histamine (or an agonist or antagonist thereof, depending on the embodiment). Therefore, in several embodiments, dosing regimens, such as the non-limiting embodiment of the dosing regimen shown in Table 3A, are directed to only a portion of the histamine receptors. For example, the non-limiting embodiment of the dosing regimen shown in Table 3A is directed to the H1, H2 and H3 receptors. In additional embodiments, however, doses and/or volumes are adjusted to enable targeting of the H4 receptor in addition to the H1, H2, and/or H3 receptors. Additionally, in some embodiments, dosing regimens target only two histamine receptors. In such embodiments, the volumes and concentrations are adjusted accordingly. For example, the non-limiting example dosing regimen in Table 3A could be adjusted to target H2 and H3 receptors.

In several embodiments, the volumes are adjusted proportionately, such that, for example, segment 1 would comprise two concentrations (one targeting each receptor) and volumes for each of 0.05 mL, thereby retaining the 0.1 mL total volume delivered. Likewise, the total volume for Segment 2 would still add up to be 0.2 mL, but would be delivered in 2 administration volumes of 0.1 mL (one for each concentration), and 0.3 mL for Segment 3 (delivered in 2 administration volumes of 0.15 mL, one for each concentration), and the like.

In several embodiments, as discussed above, doses can be administered on a compressed time scale, e.g., two, three, four (or more) doses administered within a few seconds, a few minutes, within an hour, within several hours, etc. In several embodiments, this approach advantageously reduces risk of side effects, which is particularly beneficial for individuals who are sensitive to histamine (or its agonists/antagonists). Also, in several embodiments, such a dosing regimen increases compliance because, as shown in Table 3, after the first 3 segments, each subsequent segment not only comprises a smaller number of doses, but each segment is also is administered on a compressed time frame. Thus, as an example, segment 4 is administered all within a single day (e.g., May 13) and no additional doses need be administered until 2 weeks later. The compressed dosing schedule is such that the entirety of a segment can be considered a single "dose" even though the various concentrations of histamine (or its agonists/antagonists) are administered separately (within a time frame of several seconds, e.g., within about 5 seconds, within about 10 seconds, within about 15 seconds, etc.). Additionally, as the segment number increases, the duration between segments increases, and with the compressed doses within each segment, the actual administration of histamine (or its agonist or antagonist) occurs within a very short relative period of time. As such, the treatment of histamine imbalance need not be an intrusion into the day to day lives of patients, but can be addressed in a matter of moments, once every few weeks (or longer). Lastly, the segment sequence can be rearranged, depending on the condition, in order to achieve optimum results.

TABLE 3

"Combination" Dosing Regimen for Histadelia and/or Histapenia

| Segment Number | Dose Number | Concentration | Volume | Administration Date | Dosing Frequency |
| --- | --- | --- | --- | --- | --- |
| 1 | 1 | C1 | 0.1 mL | February 4 | 2x/week |
|  | 2 | C2 | 0.1 mL | February 7 |  |
|  | 3 | C3 | 0.1 mL | February 11 |  |
|  | 4 | C4 | 0.1 mL | February 14 |  |

TABLE 3-continued

"Combination" Dosing Regimen for Histadelia and/or Histapenia

| Segment Number | Dose Number | Concentration | Volume | Administration Date | Dosing Frequency |
|---|---|---|---|---|---|
| 2 | 5 | C1 | 0.2 mL | February 18 | 1 x/week |
|   | 6 | C2 | 0.2 mL | February 25 |   |
|   | 7 | C3 | 0.2 mL | March 4 |   |
|   | 8 | C4 | 0.2 mL | March 11 |   |
| 3 | 9 | C1 | 0.3 mL | March 18 | 1 x/2 weeks |
|   | 10 | C2 | 0.3 mL | April 1 |   |
|   | 11 | C3 | 0.3 mL | April 15 |   |
|   | 12 | C4 | 0.3 mL | April 29 |   |
| 4 | 13 | C1 | 0.1 mL | May 13 | 2 weeks (+/−1 week) |
|   |   | C2 | 0.1 mL |   |   |
|   |   | C3 | 0.1 mL |   |   |
|   |   | C4 | 0.1 mL |   |   |
| 5 | 14 | C1 | 0.15 mL | June 3 | 3 weeks (+/−2 weeks) |
|   |   | C2 | 0.15 mL |   |   |
|   |   | C3 | 0.15 mL |   |   |
|   |   | C4 | 0.15 mL |   |   |
| 6 | 15 | C1 | 0.2 mL | July 1 | 4 weeks (+/−2 weeks) |
|   |   | C2 | 0.2 mL |   |   |
|   |   | C3 | 0.2 mL |   |   |
|   |   | C4 | 0.2 mL |   |   |
| 7 | 16 | C1 | 0.25 mL | August 5 | 5 weeks (+/−3 weeks) |
|   |   | C2 | 0.25 mL |   |   |
|   |   | C3 | 0.25 mL |   |   |
|   |   | C4 | 0.25 mL |   |   |
| 8 | 17 | C1 | 0.3 mL | September 9 | 6 weeks (+/−4 weeks) |
|   |   | C2 | 0.3 mL |   |   |
|   |   | C3 | 0.3 mL |   |   |
|   |   | C4 | 0.3 mL |   |   |

C1 = 1.1 ng/mL +/− 30% histamine base
C2 = 3 ng/mL +/− 50% histamine base
C3 = 1.1 µg/mL +/− 30% histamine base
C4 = 3.33 µg/mL +/− 30% histamine base

TABLE 3A

"Combination" Dosing Regimen for Histadelia and/or Histapenia

| Segment Number | Dose Number | Concentration/Volume | Administration Date | Dosing Frequency |
|---|---|---|---|---|
| 1 | 1 | C1/0.1 mL | February 4 | 2x/week |
|   | 2 | C2/0.1 mL | February 7 |   |
|   | 3 | C3/0.1 mL | February 11 |   |
|   | 4 | C4/0.1 mL | February 14 |   |
| 2 | 5 | C1/0.2 mL | February 18 | 1x/week |
|   | 6 | C2/0.2 mL | February 25 |   |
|   | 7 | C3/0.2 mL | March 4 |   |
|   | 8 | C4/0.2 mL | March 11 |   |
| 3 | 9 | C1/0.3 mL | March 18 | 1x/2 weeks |
|   | 10 | C2/0.3 mL | April 1 |   |
|   | 11 | C3/0.3 mL | April 15 |   |
|   | 12 | C4/0.3 mL | April 29 |   |
| 4 | 13 | C2/0.1 mL | May 13 | 2 weeks |
|   |   | C3/0.1 mL |   |   |
|   |   | C4/0.1 mL |   |   |
| 5 | 14 | C2/0.13 mL | June 3 | 3 weeks |
|   |   | C3/0.13 mL |   |   |
|   |   | C4/0.13 mL |   |   |
| 6 | 15 | C2/0.17 mL | July 1 | 4 weeks |
|   |   | C3/0.17 mL |   |   |
|   |   | C4/0.17 mL |   |   |
| 7 | 16 | C2/0.2 mL | August 5 | 5 weeks |
|   |   | C3/0.2 mL |   |   |
|   |   | C4/0.2 mL |   |   |
| 8 | 17 | C2/0.23 mL | September 9 | 6 weeks |
|   |   | C3/0.23 mL |   |   |
|   |   | C4/0.23 mL |   |   |
| 9 | 18 | C2/0.27 mL | October 28 | 7 weeks |
|   |   | C3/0.27 mL |   |   |
|   |   | C4/0.27 mL |   |   |
| 10 | 19 | C2/0.3 mL | December 23 | 8 weeks |
|   |   | C3/0.3 mL |   |   |
|   |   | C4/0.3 mL |   |   |
| 11 | 20 | C2/0.33 mL | February 24 | 9 weeks |
|   |   | C3/0.33 mL |   |   |
|   |   | C4/0.33 mL |   |   |

C1 = 1.0 pg/mL histamine base
C2 = 1.0 ng/mL histamine base
C3 = 1.0 µg/mL histamine base
C4 = 3.5 µg/mL histamine base The concentrations identified in Tables 3 and 3A represent "histamine base" concentrations (e.g., the amount of histamine itself). For example, in the case of histamine phosphate, two molecules of phosphoric acid are attached to each molecule of histamine. Since the molecular weight of histamine phosphate is 307.15 and that of histamine itself is 111.15, 2.75 mg of the salt are required to obtain 1 mg of active principle. The administration dates are identified as an example only. Additionally, within a segment, the administration sequence can be varied (e.g., rather than administration of C1, C2, C3 and C4, administration could be, for example C3, C3, C2 and C1) to any desired order depending on the embodiment. Further, in some embodiments, any one (or more) of segments 4, 5, 6, 7 or 8 in Table 3 or Table 3A can be inserted within any or all of segments 1, 2 and 3 (e.g., segment 4 is "nested" into segment 1)

In several embodiments, there are also provided "escalating" dosing regimens that are used to facilitate returning a patient's histamine concentrations to within optimum ranges. The method comprises, in several embodiments, administering histamine (synthetic or natural), a histamine agonist or antagonist, or a pharmaceutically acceptable salt thereof to the patient according to the non-limiting escalating dosing regimen shown in Table 4. In several embodiments, the escalating dosing regimen enables the increase of histamine levels in a patient having a histamine level below a level required for optimum histamine function (e.g., treatment of histapenia). In several embodiments, the escalating dosing regimen enables the decrease of histamine levels in a patient having histamine levels above those required for optimum histamine function (e.g., histadelia). As discussed herein, in several embodiments, the method comprises administration of histamine (synthetic or natural), a histamine agonist or antagonist, or a pharmaceutically acceptable salt thereof to the subject.

In several embodiments, the escalating dosing regimen comprises a plurality (e.g., 2, 3, 4, 5, 6, or more) of segments, each comprising, for example, a plurality of individual doses. In several embodiments, the concentration of each dose within a segment is increased with respect to the prior dose, but the volume administered is held constant across a given dosing segment while all doses are administered with a short amount of time (e.g. 5 minutes). Advantageously, should individuals have sensitivity to histamine, in several embodiments, dosing regimens, such as the non-limiting embodiment of the dosing regimen shown in Table 4, are directed to only a portion of the histamine receptors. For example, the non-limiting embodiment of the dosing regimen can be directed to the H1, H2 and H3 receptors (though additional embodiments, however, comprise adjusted concentrations and/or volumes to enable targeting of the H4 receptor in addition to the H1, H2, and/or H3 receptors). Additionally, in some embodiments, dosing regimens target only two histamine receptors. In such embodiments, the volumes and concentrations are adjusted accordingly. For example, the non-limiting example dosing regimen in Table 4 could be adjusted to target and H2 receptors or H2 and H4 receptors. In several embodiments, the volumes are adjusted proportionately, such that, for example, even with fewer doses (since only targeting 2 receptors), the total volume administered would remain as shown in Table 4.

In several embodiments, the escalating dosing regimen comprises segments having 3 individual doses per segment (see e.g., the non-limiting embodiment in Table 4A). In several embodiments, concentration 1 (C1) has been eliminated from the segments. As discussed above, in some embodiments both C1 and C2 target the H3 and/or H4 receptors. Thus, the elimination of the C1 dose, in several embodiments, prevents or otherwise reduces risk of the subject developing refractoriness to histamine and helps maintain the expression of the receptors at levels that promote proper histamine balance. Moreover, as the use of a single dose targeting the H3 and/or H4 receptors reduces risk of adverse side effects or sensitivity to histamine (or an agonist or antagonist thereof, depending on the embodiment), the escalating regimen does not employ a "loading period". Thus, the escalating dose regimen may be particularly suited to individuals with a known elevated histamine tolerance (e.g., the elimination of the loading period and elimination of the C1 dose is unlikely to induce adverse responses). Advantageously, should individuals have sensitivity to histamine, in several embodiments, dosing regimens, such as the non-limiting embodiment of the dosing regimen shown in Table 4A, are directed to only a portion of the histamine receptors. For example, the non-limiting embodiment of the dosing regimen shown in Table 4A is directed to the H1, H2 and H3 receptors (though additional embodiments, however, comprise adjusted concentrations and/or volumes to enable targeting of the H4 receptor in addition to the H1, H2, and/or H3 receptors). Additionally, in some embodiments, dosing regimens target only two histamine receptors. In such embodiments, the volumes and concentrations are adjusted accordingly. For example, the non-limiting example dosing regimen in Table 4A could be adjusted to target H1 and H2 receptors. In several embodiments, the volumes are adjusted proportionately, such that, for example, even with fewer doses (since only targeting 2 receptors), the total volume administered would remain as shown in Table 4A.

As discussed above, while the doses are administered separately, they can be considered a single "dose" because the entirety of a segment is administered on a reduced time frame (e.g., within about 5 seconds, within about 10 seconds, within about 15 seconds, etc.). Additionally, as the segment number increases, the duration between segments increases, and as such the actual administration of histamine (or its agonist or antagonist) occurs within a very short relative period of time, thereby facilitating compliance of the subject and continued maintenance of the dosing regimens.

TABLE 4

"Escalating" Dosing Regimen for Histadelia and/or Histapenia

| Segment Number | Dose Number | Concentration | Volume | Administration Date | Dosing Frequency |
|---|---|---|---|---|---|
| 1 | 1 | C1 | 0.05 mL | January 6 | 2 weeks |
|   |   | C2 | 0.05 mL |   | (+/−1 |

TABLE 4-continued

"Escalating" Dosing Regimen for Histadelia and/or Histapenia

| Segment Number | Dose Number | Concentration | Volume | Administration Date | Dosing Frequency |
|---|---|---|---|---|---|
|   |   | C3 | 0.05 mL |   | week) |
|   |   | C4 | 0.05 mL |   |   |
| 2 | 2 | C1 | 0.1 mL | January 20 | 3 week |
|   |   | C2 | 0.1 mL |   | (+/−1.5 |
|   |   | C3 | 0.1 mL |   | weeks) |
|   |   | C4 | 0.1 mL |   |   |
| 3 | 3 | C1 | 0.15 mL | February 10 | 4 weeks |
|   |   | C2 | 0.15 mL |   | (+/−2 |
|   |   | C3 | 0.15 mL |   | weeks) |
|   |   | C4 | 0.15 mL |   |   |
| 4 | 4 | C1 | 0.2 mL | March 10 | 6 weeks |
|   |   | C2 | 0.2 mL |   | (+/−3 |
|   |   | C3 | 0.2 mL |   | weeks) |
|   |   | C4 | 0.2 mL |   |   |
| 5 | 5 | C1 | 0.25 mL | April 21 | 8 weeks |
|   |   | C2 | 0.25 mL |   | (+/−4 |
|   |   | C3 | 0.25 mL |   | weeks) |
|   |   | C4 | 0.25 mL |   |   |
| 6 | 6 | C1 | 0.3 mL | June 16 | 10 weeks |
|   |   | C2 | 0.3 mL |   | (+/−5 |
|   |   | C3 | 0.3 mL |   | weeks) |
|   |   | C4 | 0.3 mL |   |   |

C1 = 1.1 ng/mL +/− 30% histamine base
C2 = 3 ng/mL +/− 50% histamine base
C3 = 1.1 µg/mL +/− 30% histamine base
C4 = 3.33 µg/mL +/− 30% histamine base

TABLE 4A

"Escalating" Dosing Regimen for Histadelia and/or Histapenia

| Segment Number | Dose Number | Concentration/Volume | Administration Date | Dosing Frequency |
|---|---|---|---|---|
| 1 | 1 | C2/0.03 mL<br>C3/0.03 mL<br>C4/0.03 mL | January 6 |   |
| 2 | 2 | C2/0.07 mL<br>C3/0.07 mL<br>C4/0.07 mL | January 13 | 1 week |
| 3 | 3 | C2/0.1 mL<br>C3/0.1 mL<br>C4/0.1 mL | January 27 | 2 weeks |
| 4 | 4 | C2/0.13 mL<br>C3/0.13 mL<br>C4/0.13 mL | February 17 | 3 weeks |
| 5 | 5 | C2/0.17 mL<br>C3/0.17 mL<br>C4/0.17 mL | March 17 | 4 weeks |
| 6 | 6 | C2/0.2 mL<br>C3/0.2 mL<br>C4/0.2 mL | April 21 | 5 weeks |
| 7 | 7 | C2/0.23 mL<br>C3/0.23 mL<br>C4/0.23 mL | June 2 | 6 weeks |
| 8 | 8 | C2/0.27 mL<br>C3/0.27 mL<br>C4/0.27 mL | July 21 | 7 weeks |
| 9 | 9 | C2/0.33 mL<br>C3/0.3 mL<br>C4/0.3 mL | September 15 | 8 weeks |
| 10 | 10 | C2/0.33 mL<br>C3/0.33 mL<br>C4/0.33 mL | November 17 | 9 weeks |

C1 = 1.0 pg/mL histamine base
C2 = 1.0 ng/mL histamine base
C3 = 1.0 µg/mL histamine base
C4 = 3.5 µg/mL histamine base The concentrations identified in Table 4 and Table 4A represent "histamine base" concentrations (e.g., the amount of histamine itself). For example, in the case of histamine phosphate, two molecules of phosphoric acid are attached to each molecule of histamine. Since the molecular weight of histamine phosphate is 307.15 and that of histamine itself is 111.15, 2.75 mg of the salt are required to obtain 1 mg of active principle. As with other tables, the dates provides on the table are for guidance only (e.g., to represent time intervals as opposed to actual dates). Additionally, within a segment, the administration sequence can be varied (e.g., rather than administration of C1, C2, C3 and C4, administration could be, for example C3, C3, C2 and C1) to any desired order depending on the embodiment.

There is provided, in several embodiments of the invention, a histamine receptor activator (e.g., histamine) for use in the treatment of patients showing an elevated amount of circulating histamine or in patients showing a reduced amount of circulating histamine, such patients being afflicted with migraine headaches, Parkinson's Disease, Alzheimer's Disease, coronary disease, leukemia, amyotrophic lateral sclerosis, epilepsy, histadelia and/or histapenia. Also provided is a histamine receptor activator for use in the treatment of migraine headaches, Parkinson's Disease, Alzheimer's Disease, coronary disease, leukemia, amyotrophic lateral sclerosis, epilepsy, histadelia and/or histapenia with associated restoration of histamine balance. Some embodiments of the invention comprise a histamine receptor activator for use in the treatment of diseases associated with the over-expression and/or over-activity of the histamine H1 receptor and/or for use in the treatment of diseases associated with the under-expression and/or under-activity one or more of the histamine H2, H3, and/or H4 receptors.

As discussed above, the treatment according to the methods disclosed herein may be based on clinical assessment that a patient is suffering from histapenia or histadelia, such as by a diagnostic assay indicating the presence of histamine levels above or below standard plasma histamine levels or standard urine histamine levels. For example, histamine levels in the range of 45 to about 50 ng/ml of plasma are used as an indicator for optimum histamine function in some embodiments, and plasma levels above or below this range indicate that the patient may benefit from the methods disclosed herein.

Dietary supplements are also optionally used, in several embodiments to facilitate rebalance of histamine. For example, in several embodiments, supplements that help promote methylation of histamine (e.g., to facilitate metabolism of histamine) are optionally used to supplement certain of the methods disclosed herein for treating histadelia). Methylation-promoting supplements include, but are not limited to, S-adenosylmethionine (SAM-e), methyl-B12, and trimethylglycine (TMG), dimethylglycine (DMG), or combinations thereof. Additionally, calcium (which helps mobilize histamine into the bloodstream) and/or vitamin C (which facilitates excretion of histamine) supplements can be used to help reduce histamine, in conjunction with the dosing regimens disclosed herein. Magnesium supplementation is used, in several embodiments, to facilitate stabilization of mast cells (thereby reducing degranulation and histamine release). Low-histamine diets are also used in certain embodiments wherein a reduction in histamine is desired. Also, copper is associated with the enzymes that degrade histamine, thus, in several embodiments, reduction in dietary copper intake is beneficial in treating histapenia.

Histamine Compositions and Administration

In several embodiments, histamine is administered as a pharmaceutically acceptable salt. In several embodiments, the diphosphate ($H_3PO_4$) salt of histamine is employed. In several embodiments, histamine phosphate is used. Other salts may also be used, including but not limited to, acid addition salts formed with inorganic acids such as hydrochloric acid (e.g., histamine dihydrochloride), hydrobromic acid, sulfuric acid, nitric acid, phosphoric acid, and the like, or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like, as well as combinations thereof.

In addition, in several embodiments, pharmaceutically acceptable salts of histamine can be formed when an acidic proton present is capable of reacting with inorganic or organic bases. Acceptable inorganic bases include, but are not limited to, sodium hydroxide, sodium carbonate, potassium hydroxide, aluminum hydroxide and calcium hydroxide. Acceptable organic bases include, but are not limited to, ethanolamine, diethanolamine, triethanolamine, tromethamine, N-methylglucamine and the like.

As used, herein the term "pharmaceutically acceptable" shall be given its ordinary meaning and shall also include components, compounds, chemicals, etc. useful in the preparation of a pharmaceutical composition that is generally safe, non-toxic and neither biologically nor otherwise undesirable and includes that which is acceptable for veterinary use as well as human pharmaceutical use. As used, herein, the term "pharmaceutically acceptable salts" shall be given its ordinary meaning and shall include salts of compounds that are pharmaceutically acceptable, as defined above, and/or that possess the desired pharmacological activity.

In several embodiments, the methods employ a comprise administration of one or more agonist and/or antagonist compounds. Depending on the embodiments the agonist or antagonist may be administered in order to increase or decrease the function of a particular histamine receptor. For example, in several embodiments an H3R agonist may be administered, while in some embodiments, an H1R antagonist is administered. The agonists may be superagonists, full agonists, partial agonists, or inverse agonists. Antagonists, depending on the embodiment, can be competitive, non-competitive, uncompetitive, or silent antagonists. The agonists and antagonists can also be either selective or nonselective, depending on the embodiment. In several embodiments, the use of one or more agonist or antagonist compounds is in addition to use of anther therapeutic agent (e.g., histamine).

In several embodiments, the methods optionally comprise administration of an antihistamine compound. For example, in several embodiments an antagonist of the H1 receptor is administered in conjunction with the histamine dosing regimen, and the reduction of H1 receptor activity by the antagonist further potentiates the suppressive effects of the H2/H3 receptors. For example, H1 antagonists that may be used include, but are not limited to aceprometazine, acrivastine, alcaftadine, alimemazine, antazoline, aptazapine, astemizole, azatadine, azelastine, bamipine, bepotastine, bilastine, bisulepine, bromazine, brompheniramine, carbinoxamine, carbinoxamine/pseudoephedrine, cetirizine, chlorcyclizine, chloropyramine, chlorothen, chlorphenamine, chlorphenoxamine, cinnarizine, clemastine, clemizole, clobenzepam, clobenztropine, clocinizine, cyanodothiepin, cyclizine, cyproheptadine, dacemazine, deptropine, desloratadine, dexbrompheniramine, dexchlorpheniramine, dimenhydrinate, dimetindene, diphenhydramine, diphenylpyraline, doxylamine, drixoral, ebastine, embramine, emedastine, epinastine, esmirtazapine, etymemazine, fexofenadine, histapyrrodine, homochlorcyclizine, hydroxyethylpromethazine, hydroxyzine, hydroxyzine, isopromethazine, isothipendyl, ketotifen, latrepirdine, levocabastine, levocetirizine, loratadine, mebhydrolin, mepyramine, methafurylene, methapyrilene, methdilazine, 4-methyldiphenhydramine, mianserin, mirtazapine, mizolastine, moxastine, olopatadine, orphenadrine, oxatomide, pemirolast, phenindamine, pheniramine, phenyltoloxamine, pirolate, promethazine, propiomazine, pseudoephedrine/loratadine, pyrrobutamine, repirinast, resporal, rupatadine, setastine, setiptiline, talastine, terfenadine, thenalidine, thenyldiamine, thiazinamium metilsulfate, thonzylamine, tolpropamine, toplexil, tripelennamine, triprolidine, and combinations thereof. In other embodiments, agonist compounds may be used (e.g., depending on whether a subject is affected with histapenia or histadelia). In some embodiments, H1 agonists may be used, such as for example, when treating a subject with histapenia. Suitable H1 agonists include, but are not limited to 2-Pyridylethylamine dihydrochloride, Histamine trifluoromethyl toluidide, as well as the various salts of histamine (either synthetic or naturally occurring) disclosed herein, or combinations thereof.

In several embodiments, agonists of the H2R are used, including, but not limited to, for example, arpromidine, amthamine, impromidine, dimaprit, sopromidine, 4-methylhistamine, and combinations thereof. Also, in several embodiments, H2R antagonists are used, including, but not limited to, for example, cimetidine, mifentidine, nizatidine, ranitidine, titotidine, famotidine, zolantidine, iodoaminopotentidine, compound SKF 92857, mepyramine, loxtidine, and combinations thereof H3 receptor agonists are used in several embodiments. Suitable H3R agonists include, but are not limited to (R)-α-methylhistamine, cipralisant, immepip, imetit, immethridine, methimepip, proxyfan, and combinations thereof. Conversely, H3R antagonists may be used, depending on the embodiment. Suitable H3R antagonists include, but are not limited to A-349,821, ABT-239, betahistine, burimamide, ciproxifan, conessine, clobenpropit, impentamine, iodophenpropit, thioperamide, VUF-5681 (4-[3-(1H-Imidazol-4-yl)propyl]piperidine), and combinations thereof.

H4 receptor agonists are used in several embodiments. Suitable H4R agonists include, but are not limited to VUF-8430 (2-[(aminoiminomethyl)amino]ethyl carbamimidothioic acid ester), OUP-16, 4-methylhistamine, and the various salts of histamine (either synthetic or naturally occurring) disclosed herein, or combinations thereof. H4R antagonists may be used, depending on the embodiment. Suitable H4R antagonists include, but are not limited to thioperamide, JNJ 7777120, VUF-6002 (1-[(5-chloro-1H-benzimidazol-2-yl) carbonyl]-4-methylpiperazine), A987306, A943931, and combinations thereof.

In several embodiments, the invention comprises a histamine receptor activator for use in the treatment of migraine headaches, Parkinson's Disease, Alzheimer's Disease, coronary disease, leukemia, amyotrophic lateral sclerosis, epilepsy, histadelia and/or histapenia by inhibiting the activity and/or expression of a histamine receptor selected from the group consisting of the histamine H1 receptor, the histamine H2 receptor, the histamine H3 receptor, and the histamine H4 receptor. In several embodiments, the histamine receptor activator inhibits the activity and/or expression of the histamine H1 receptor and thus is beneficial for use in the treatment of diseases associated with the over-expression and/or over-activity of the histamine H1 receptor. Moreover, in several embodiments, the histamine receptor activator (or activators) are for use in the treatment of diseases associated with the under-expression and/or under-activity one or more of the histamine H2, H3, and/or H4 receptors.

In several embodiments, the invention comprises a histamine receptor activator for use in the treatment of migraine headaches, Parkinson's Disease, Alzheimer's Disease, coronary disease, leukemia, amyotrophic lateral sclerosis, epilepsy, histadelia and/or histapenia by combined, sequential, or separate administration with a complete or partial antagonist of a histamine H1 receptor. Moreover, in several embodiments, the invention comprises an inhibitor of the activity and/or expression of a histamine H1 receptor for use in the treatment of migraine headaches, Parkinson's Disease, Alzheimer's Disease, coronary disease, leukemia, amyotrophic lateral sclerosis and/or epilepsy.

Depending on the embodiment, the histamine compositions used in the methods disclosed herein can be used in one or more of a variety of forms, depending on the route of administration. Administration can be, for example oral, ophthalmic, otologic, and/or nasal, urogenital, rectal, transdermal, via implantation, transdermal, inhalation and/or via infusion. Patches may be used in one embodiment. Oral delivery can be, for example, enteral (e.g., to the digestive tract), buccal (e.g., sublingual), and/or inhaled (e.g., to the respiratory tract). Depending on the embodiment, oral forms include, but are not limited to liquid, solid, and/or semi-solid forms. In several embodiments, enteral administration is by way of administration of one or more of pills, tablets, capsules, gel-caps, (including timed release forms) osmotic delivery systems, elixirs, suspension, syrup, emulsions, hydrogels, wafer, molecular encapsulation forms, softgels, solution, suspensions, syrups, tinctures, and/or tisanes. Buccal administration, in several embodiments, is by way of administration of one or more of orally disintegrating tablets or pills, films, lozenges, chewing gums, popsicles, lollipops, mouthwashes, mouth rinses, toothpaste, ointment, and/or oral sprays.

In several embodiments, oral forms may include one or more inert diluent and/or an edible carrier. For example, the compositions may be enclosed in gelatin capsules (for oral use) or compressed into tablets (for oral or buccal use) or formulated into troches or sublingual liquids (for buccal use). In several embodiments, the active histamine compound can be incorporated with excipients and and/or various pharmaceutically compatible carriers, binding agents, and/or adjuvant materials. Oral forms, may, depending on the embodiment, contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a gliding such as colloidal silicon dioxide; a sweetening agent such as sucrose or saccharin; or a flavoring agent or agents such as mint, methyl salicylate, or fruit flavors, candy flavors, combinations of flavors, etc. When the dosage unit form is a capsule, it can optionally contain, in addition to material of the above type, a liquid carrier such as a fatty oil. In addition, dosage unit forms can contain various other materials which modify the physical form of the dosage unit, for example, coatings of sugar, shellac, or other enteric agents. Administration to the respiratory tract, in several embodiments, is by way of administration of one or more of a dry powder inhaler, nebulize, vaporizer, metered dose-inhaler, respiratory mask, oxygen concentrator, nasal cannula, and the like.

Ophthalmic, otologic, and/or nasal administration are used in several embodiments, and in some such embodiments are advantageous because of the rapid absorption of the histamine compositions through, for example, the mucous membranes. Forms for delivery via the eye, nose, or ear include, but are not limited to, for example, nasal spray, ear drops, eye drops, ointments, hydrogels, nanosphere suspensions or emulsions, mucoadhesive microdisc (e.g., microsphere tablets) and the like.

Urogenital and/or rectal administration forms include, but are not limited to ointments, pessary (e.g., vaginal suppository), vaginal rings, vaginal douches, intrauterine devices (IUD), extra-amniotic infusions, intravesical infusions, suppositories, enema, and/or Murphy drip, etc.

Dermal administration forms, depending on the embodiment, include, but are not limited to ointments, liniments, pastes, films, hydrogels, liposomes, transfersome vesicles, creams, lotion, balms, salves, shampoos, dermal patches (e.g., transdermal patch), transdermal spray, direct or jet injector, etc.

Injection or infusion may also be used, depending on the embodiment. For example, delivery of histamine can be intradermal, subcutaneous, via a transdermal implant, intravenous, intramuscular, intraperitoneal, intraarterial, intracavernous, intracerebral, intrathecal, epidural, and the like.

In several embodiments, the therapeutic agent is self-administered. In some embodiments, the therapeutic agent is administered to a subject in need thereof by a non-medical professional (an individual who is not a medical professional, such as for example, an acquaintance, family member, spouse, etc.).

Combinations of the various administration routes are also used, in several embodiments. For example, an oral medication can be used in conjunction with a subcutaneous administration. Likewise, both intramuscular and subcutaneous administration routes are optionally employed, for example. Solutions or suspensions used for injection or infusion can optionally include one or more of the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride, mannitol and dextrose. Depending on the embodiments, an injectable preparation can optionally be enclosed in ampoules, disposable syringes or multiple dose vials made of glass or plastic, or other suitable material. When used in conjunction with histamine compositions as disclosed herein, antihistamines may also be in any of the above forms.

Concentrations and dosages provided in the examples below and the tables above are for a subject weight of 75-85 kg and can be adjusted proportionally for different weights according to several embodiments. In several embodiments, kits comprising pre-filled syringes, vials or other containers are provided with the doses of therapeutic agent described herein. Instructions for use, including for example a paper or electronic calendar system or other alert for scheduling self-treatment, are provided in one embodiment.

EXAMPLES

The examples provided herein are non-limiting examples of some embodiments of the invention.

Example 1

Histamine Dosing Regimen for Treatment of Neurological Disorders

In several embodiments, a histamine dosing regimen according to the methods disclosed above is used for the reduction and/or prevention of neurological disorders, including migraine headaches, Parkinson's and Alzheimer's and ALS and epilepsy. A long-term migraine sufferer was treated with the regimen shown in Table 5 (administration dates identified as an example only). Histamine was administered subcutaneously according to the indicated times and concentrations.

TABLE 5

| Dosing Regimen for Histadelia and/or Histapenia | | | | | |
|---|---|---|---|---|---|
| Segment Number | Dose Number | Concentration/ Volume | Target Receptor | Administration Date | Dosing Frequency |
| 1 | 1 | C1/0.1 mL | H3 | February 4 | 2x/week |
|   | 2 | C2/0.1 mL | H4 | February 7 |   |
|   | 3 | C3/0.1 mL | H1 | February 11 |   |
|   | 4 | C4/0.1 mL | H2 | February 14 |   |
| 2 | 5 | C1/0.2 mL | H3 | February 18 | 1x/week |
|   | 6 | C2/0.2 mL | H4 | February 25 |   |
|   | 7 | C3/0.2 mL | H1 | March 4 |   |
|   | 8 | C4/0.2 mL | H2 | March 11 |   |
| 3 | 9 | C1/0.3 mL | H3 | March 18 | 1x/10 days |
|   | 10 | C2/0.3 mL | H4 | March 28 |   |
|   | 11 | C3/0.3 mL | H1 | April 7 |   |
|   | 12 | C4/0.3 mL | H2 | April 17 |   |
| 4 | 13 | C1/0.4 mL | H3 | April 27 | 1x/2 weeks |
|   | 14 | C2/0.4 mL | H4 | May 11 |   |
|   | 15 | C3/0.4 mL | H1 | May 25 |   |
|   | 16 | C4/0.4 mL | H2 | June 8 |   |

TABLE 5-continued

Dosing Regimen for Histadelia and/or Histapenia

| Segment Number | Dose Number | Concentration/ Volume | Target Receptor | Administration Date | Dosing Frequency |
|---|---|---|---|---|---|
| 5 | 17 | C1/0.5 mL | H3 | June 22 | 1x/3 weeks |
|   | 18 | C2/0.5 mL | H4 | July 13 |   |
|   | 19 | C3/0.5 mL | H1 | August 3 |   |
|   | 20 | C4/0.5 mL | H2 | August 24 |   |

C1 = 1.1 ng/mL +/− 30% histamine base
C2 = 3 ng/mL +/− 50% histamine base
C3 = 1.1 µg/mL +/− 30% histamine base
C4 = 3.33 µg/mL +/− 30% histamine base Another possible regimen in accordance with several embodiments is shown in Table 5A (administration dates identified as an example only).

TABLE 5A

Dosing Regimen for Histadelia and/or Histapenia

| Segment Number | Dose Number | Concentration/ Volume | Target Receptor | Administration Date | Dosing Frequency |
|---|---|---|---|---|---|
| 1 | 1 | C1/0.1 mL | H3/H4 | February 4 | 2x/week |
|   | 2 | C2/0.1 mL | H3/H4 | February 7 |   |
|   | 3 | C3/0.1 mL | H1 | February 11 |   |
|   | 4 | C4/0.1 mL | H2 | February 14 |   |
| 2 | 5 | C1/0.2 mL | H3/H4 | February 18 | 1x/week |
|   | 6 | C2/0.2 mL | H3/H4 | February 25 |   |
|   | 7 | C3/0.2 mL | H1 | March 4 |   |
|   | 8 | C4/0.2 mL | H2 | March 11 |   |
| 3 | 9 | C1/0.3 mL | H3/H4 | March 18 | 1x/10 days |
|   | 10 | C2/0.3 mL | H3/H4 | March 28 |   |
|   | 11 | C3/0.3 mL | H1 | April 7 |   |
|   | 12 | C4/0.3 mL | H2 | April 17 |   |
| 4 | 13 | C1/0.4 mL | H3/H4 | April 27 | 1x/2 weeks |
|   | 14 | C2/0.4 mL | H3/H4 | May 11 |   |
|   | 15 | C3/0.4 mL | H1 | May 25 |   |
|   | 16 | C4/0.4 mL | H2 | June 8 |   |
| 5 | 17 | C1/0.5 mL | H3/H4 | June 22 | 1x/3 weeks |
|   | 18 | C2/0.5 mL | H3/H4 | July 13 |   |
|   | 19 | C3/0.5 mL | H1 | August 3 |   |
|   | 20 | C4/0.5 mL | H2 | August 24 |   |

C1 = 1.0 pg/mL histamine base
C2 = 1.0 ng/mL histamine base
C3 = 1.0 µg/mL histamine base
C4 = 3.5 µg/mL histamine base The concentrations identified in Table 5 and Table 5A represent "histamine base" concentrations (e.g., the amount of histamine itself). For example, in the case of histamine phosphate, two molecules of phosphoric acid are attached to each molecule of histamine. Since the molecular weight of histamine phosphate is 307.15 and that of histamine itself is 111.15, 2.75 mg of the salt are required to obtain 1 mg of active principle. Additionally, within a segment, the administration sequence can be varied (e.g., rather than administration of C1, C2, C3 and C4, administration could be, for example C3, C3, C2 and C1) to any desired order depending on the embodiment.

As a result of the histamine dosing regimen above, the subject (a migraine suffer for over 35 years) experienced a significant reduction in frequency of migraine episodes, as well as a reduction in intensity of migraines when they did occur. Prior to the dosing regimen, the subject experienced about 3-5 migraines per week, on average. This frequency was despite the use of various prescription drugs, over the counter drugs, dietary changes, and/or alternative medicine approaches. Migraine events resulted in numerous missed work days, and reduced work efficiency. Migraines also caused loss of certain occupational promotional opportunities and, outside of work, loss of the ability to exercise (as physical exertion triggered migraine attacks). Overall the migraine events led to a consistent decline in quality of life.

As a result of implementing the above mentioned histamine dosing regimen, the intensity and frequency of migraines has been drastically reduced in this subject, who currently experiences approximately only 1 migraine every 2 months. Drastically improved quality of life has resulted, as has the subject's ability to spend interactive time with the subject's family, being able to participate in family and social events, being able to exercise and becoming a productive member of society. This regimen also resulted in limited side effects associated with the regimen (e.g., no histamine-induced headaches). After segment 5 was completed, the subject restarted the dosing regimen at segment 1 after a period of time had elapsed. As discussed above, the prevalence of histamine in various physiological functions, and histamine imbalance in a variety of diseases and/or disorders make several embodiments of the invention useful for treatment of other diseases and/or disorders including, but not limited to Parkinson's disease, Alzheimer's disease, epilepsy, ALS, and other disorders disclosed herein. In some embodiments, one or more segment durations may be compressed or expanded by e.g., 50% to 99% (e.g., 60%, 75%, 85%, 90%, 95%).

Example 2

Extended Histamine Dosing Regimen for Treatment

In several embodiments, an extended histamine dosing regimen is used for the reduction and/or prevention of neurological disorders, including migraine headaches, Parkinson's and Alzheimer's, coronary disease, leukemia, ALS, epilepsy, histadelia and/or histapenia (among others).

TABLE 6

Extended Dosing Regimen

| Segment Number | Dose Number | Concentration/ Volume | Time Interval |
| --- | --- | --- | --- |
| 1 | 1 | C1/0.1 mL | 1 day to 2 weeks |
|   | 2 | C2/0.1 mL | 1 day to 2 weeks |
|   | 3 | C3/0.1 mL | 1 day to 2 weeks |
|   | 4 | C4/0.1 mL | 1 day to 2 weeks |
| 2 | 5 | C1/0.2 mL | 3 days to 3 weeks |
|   | 6 | C2/0.2 mL | 3 days to 3 weeks |
|   | 7 | C3/0.2 mL | 3 days to 3 weeks |
|   | 8 | C4/0.2 mL | 3 days to 3 weeks |
| 3 | 9 | C1/0.3 mL | 1 week to 4 weeks |
|   | 10 | C2/0.3 mL | 1 week to 4 weeks |
|   | 11 | C3/0.3 mL | 1 week to 4 weeks |
|   | 12 | C4/0.3 mL | 1 week to 4 weeks |
| 4 | 13 | C1/0.4 mL | 2 weeks to 5 weeks |
|   | 14 | C2/0.4 mL | 2 weeks to 5 weeks |
|   | 15 | C3/0.4 mL | 2 weeks to 5 weeks |
|   | 16 | C4/0.4 mL | 2 weeks to 5 weeks |
| 5 | 17 | C1/0.5 mL | 3 weeks to 6 weeks |
|   | 18 | C2/0.5 mL | 3 weeks to 6 weeks |
|   | 19 | C3/0.5 mL | 3 weeks to 6 weeks |
|   | 20 | C4/0.5 mL | 3 weeks to 6 weeks |
| 6 | 21 | C1/0.6 mL | 4 weeks to 7 weeks |
|   | 22 | C2/0.6 mL | 4 weeks to 7 weeks |
|   | 23 | C3/0.6 mL | 4 weeks to 7 weeks |
|   | 24 | C4/0.6 mL | 4 weeks to 7 weeks |
| 7 | 25 | C1/0.7 mL | 5 weeks to 8 weeks |
|   | 26 | C2/0.7 mL | 5 weeks to 8 weeks |
|   | 27 | C3/0.7 mL | 5 weeks to 8 weeks |
|   | 28 | C4/0.7 mL | 5 weeks to 8 weeks |
| 8 | 29 | C1/0.8 mL | 6 weeks to 9 weeks |
|   | 30 | C2/0.8 mL | 6 weeks to 9 weeks |
|   | 31 | C3/0.8 mL | 6 weeks to 9 weeks |
|   | 32 | C3/0.8 mL | 6 weeks to 9 weeks |
| 9 | 33 | C1/0.9 mL | 7 weeks to 10 weeks |
|   | 34 | C2/0.9 mL | 7 weeks to 10 weeks |
|   | 35 | C3/0.9 mL | 7 weeks to 10 weeks |
|   | 36 | C4/0.9 mL | 7 weeks to 10 weeks |
| 10 | 37 | C1/1.0 mL | 8 weeks to 12 weeks |
|   | 38 | C2/1.0 mL | 8 weeks to 12 weeks |
|   | 39 | C3/1.0 mL | 8 weeks to 12 weeks |
|   | 40 | C4/1.0 mL | 8 weeks to 12 weeks |

C1 = 1.1 ng/mL +/− 30% histamine base
C2 = 3 ng/mL +/− 50% histamine base
C3 = 1.1 µg/mL +/− 30% histamine base
C4 = 3.33 µg/mL +/− 30% histamine base The concentrations identified in Table 6 represent "histamine base" concentrations (e.g., the amount of histamine itself). For example, in the case of histamine phosphate, two molecules of phosphoric acid are attached to each molecule of histamine. Since the molecular weight of histamine phosphate is 307.15 and that of histamine itself is 111.15, 2.75 mg of the salt are required to obtain 1 mg of active principle. In some embodiments, one or more segment durations may be compressed or expanded by e.g., 50% to 99% (e.g., 60%, 75%, 85%, 90%, 95%). Other histamine compounds may be used instead of or in addition to histamine phosphate. Additionally, within a segment, the administration sequence can be varied (e.g., rather than administration of C1, C2, C3 and C4, administration could be, for example C3, C3, C2 and C1) to any desired order depending on the embodiment.

Example 3

Extended Histamine Dosing Regimen

In several embodiments, an extended histamine dosing regimen is used for the reduction and/or prevention of neurological disorders, including migraine headaches, Parkinson's and Alzheimer's, ALS epilepsy, histadelia and/or histapenia, among others.

TABLE 7

Extended Dosing Regimen for Histadelia and/or Histapenia

| Segment Number | Dose Number | Concentration/ Volume | Time Interval |
| --- | --- | --- | --- |
| 1 | 1 | C1/0.1 mL | 1 day to 2 weeks |
|   | 2 | C2/0.1 mL | 1 day to 2 weeks |
|   | 3 | C3/0.1 mL | 1 day to 2 weeks |
|   | 4 | C4/0.1 mL | 1 day to 2 weeks |
| 2 | 5 | C1/0.2 mL | 3 days to 3 weeks |
|   | 6 | C2/0.2 mL | 3 days to 3 weeks |
|   | 7 | C3/0.2 mL | 3 days to 3 weeks |
|   | 8 | C4/0.2 mL | 3 days to 3 weeks |
| 3 | 9 | C1/0.3 mL | 1 week to 4 weeks |
|   | 10 | C2/0.3 mL | 1 week to 4 weeks |
|   | 11 | C3/0.3 mL | 1 week to 4 weeks |
|   | 12 | C4/0.3 mL | 1 week to 4 weeks |
| 4 | 13 | C1/0.4 mL | 2 weeks to 5 weeks |
|   | 14 | C2/0.4 mL | 2 weeks to 5 weeks |
|   | 15 | C3/0.4 mL | 2 weeks to 5 weeks |
|   | 16 | C4/0.4 mL | 2 weeks to 5 weeks |
| 5 | 17 | C1/0.5 mL | 3 weeks to 6 weeks |
|   | 18 | C2/0.5 mL | 3 weeks to 6 weeks |
|   | 19 | C3/0.5 mL | 3 weeks to 6 weeks |
|   | 20 | C4/0.5 mL | 3 weeks to 6 weeks |
| 6 | 21 | C1/0.6 mL | 4 weeks to 7 weeks |
|   | 22 | C2/0.6 mL | 4 weeks to 7 weeks |
|   | 23 | C3/0.6 mL | 4 weeks to 7 weeks |
|   | 24 | C4/0.6 mL | 4 weeks to 7 weeks |
| 7 | 25 | C1/0.7 mL | 5 weeks to 8 weeks |
|   | 26 | C2/0.7 mL | 5 weeks to 8 weeks |
|   | 27 | C3/0.7 mL | 5 weeks to 8 weeks |
|   | 28 | C4/0.7 mL | 5 weeks to 8 weeks |
| 8 | 29 | C1/0.8 mL | 6 weeks to 9 weeks |
|   | 30 | C2/0.8 mL | 6 weeks to 9 weeks |
|   | 31 | C3/0.8 mL | 6 weeks to 9 weeks |
|   | 32 | C3/0.8 mL | 6 weeks to 9 weeks |
| 9 | 33 | C1/0.9 mL | 7 weeks to 10 weeks |
|   | 34 | C2/0.9 mL | 7 weeks to 10 weeks |
|   | 35 | C3/0.9 mL | 7 weeks to 10 weeks |
|   | 36 | C4/0.9 mL | 7 weeks to 10 weeks |
| 10 | 37 | C1/1.0 mL | 8 weeks to 12 weeks |
|   | 38 | C2/1.0 mL | 8 weeks to 12 weeks |
|   | 39 | C3/1.0 mL | 8 weeks to 12 weeks |
|   | 40 | C4/1.0 mL | 8 weeks to 12 weeks |

C1 = 1.0 pg/mL histamine base
C2 = 1.0 ng/mL histamine base
C3 = 1.0 µg/mL histamine base
C4 = 3.5 µg/mL histamine base The concentrations identified in Table 7 represent "histamine base" concentrations (e.g., the amount of histamine itself). For example, in the case of histamine phosphate, two molecules of phosphoric acid are attached to each molecule of histamine. Since the molecular weight of histamine phosphate is 307.15 and that of histamine itself is 111.15, 2.75 mg of the salt are required to obtain 1 mg of active principle. In some embodiments, one or more segment durations may be compressed or expanded by e.g., 50% to 99% (e.g., 60%, 75%, 85%, 90%, 95%). Other histamine compounds may be used instead of or in addition to histamine phosphate. Additionally, within a segment, the administration sequence can be varied (e.g., rather than administration of C1, C2, C3 and C4, administration could be, for example C3, C3, C2 and C1) to any desired order depending on the embodiment.

Example 4

Representative Formulation

A representative formulation for use in several embodiments of the histamine dosing regimens disclosed herein is a formulation suitable for subcutaneous injection comprising, histamine base 1 mg/mL (histamine phosphate 2.75 mg/mL) in glycerin 50% (v/v). As disclosed herein, other histamine receptor activators can be used instead of or in addition to histamine phosphate. Moreover, other diluents/carriers can be used instead of, or in addition to glycerin (e.g., saline, sterile water, etc.).

Although the examples above and several embodiments discuss the histamine system, the approaches described herein may be used to rebalance other systems. For example, in some embodiments, therapeutic agents include agents that affect neurotransmission, such as agents that affect one or more of the dopamine, noradrenaline, serotonin, GABA and acetylcholine systems. The targeted and controlled pattern of receptor modulation may be particularly effective for neurological disorders. Thus, agonists and antagonists of these neurotransmission pathways, according to the approaches described herein, are encompassed within this disclosure.

When the singular forms "a," "an" and "the" or like terms are used herein, they will be understood to include plural referents unless the context clearly dictates otherwise. Thus, for example, reference to "an agent" includes two or more agents, and the like. The word "or" or like terms as used herein means any one member of a particular list and also includes any combination of members of that list.

Throughout the description and claims of this specification, the word "comprise" and variations of the word, such as "comprising" and "comprises," means "including but not limited to," and is not intended to exclude, for example, other additives, components, integers or steps.

It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "administering histamine" include "instructing the administration of histamine." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 3 mm" includes "3 mm."

What is claimed is:

1. A method for restoring histamine balance in a subject through the administration of a histamine receptor activator composition, comprising:
    administering to the subject a first administration of a first dose of a histamine receptor activator composition, wherein the histamine receptor activator comprises a histamine salt selected from the group consisting of histamine diphosphate, histamine phosphate, and histamine dihydrochloride;
    administering to the subject a first administration of a second dose of the histamine receptor activator composition,
    wherein the first administration of the first and second doses are separated by a first time interval,
        wherein the second dose of the first administration has a concentration of said histamine receptor activator composition that is greater than the concentration of the first dose of said histamine receptor activator composition and an administered volume that is the same as an administered volume of the first dose;
    administering to said subject a second administration of the first dose of the histamine receptor activator composition; and
    administering to said subject a second administration of the second dose of the histamine receptor activator composition,
    wherein the second administration of the first and second doses are separated by a second time interval,
        wherein the second dose of the second administration has a concentration of said histamine receptor activator composition that is greater than the concentration of the first dose of said histamine receptor activator composition and an administered volume that is the same as an administered volume of the first dose; and
        wherein the repeated administration of the first and second doses of the histamine receptor activator composition normalizes an activity of one or more histamine receptors of the subject, thereby restoring histamine balance.

2. The method of claim 1, further comprising at least a third administration of the first dose of the histamine receptor activator composition and at least a third administration of the second dose of the histamine receptor activator composition.

3. The method of claim 1, wherein the restoration of histamine balance treats one or more of histadelia, histapenia, migraine headaches, Parkinson's Disease, Alzheimer's Disease, amyotrophic lateral sclerosis and epilepsy.

4. The method of claim 1, wherein the first dose of the histamine receptor activator composition is administered subcutaneously at a concentration configured to activate one or more of a histamine H3 receptor and a histamine H4 receptor, and wherein the second dose of the histamine receptor activator composition is administered subcutaneously at a concentration configured to activate one or more of a histamine H1 receptor and a histamine H2 receptor.

5. The method of claim 1, wherein the administering comprises administration via a route selected from the group consisting of subcutaneous injection, intravenous injection, intraarterial injection, intramuscular injection, oral delivery, transdermal delivery, sublingual delivery, infusion, suppository, and inhalation delivery.

6. The method of claim 1, wherein said subject is susceptible to migraine headaches as a result of histamine imbalance and the restored histamine balance leads to a reduction in frequency and/or intensity of migraine headaches.

7. The method of claim 1, wherein the first time interval is equal to the second time interval.

8. The method of claim 1, wherein the first dose of said histamine receptor activator composition has a concentration of histamine receptor activator ranging from between about 0.1 ng/mL to about 10 ng/mL, wherein the second dose of the histamine receptor activator composition has a concentration of histamine receptor activator ranging from between about 0.35 µg/mL to about 10 µg/mL.

9. The method of claim 1, wherein the first time interval results in an administration frequency of between one and three times per week.

10. The method of claim 1, further comprising administering an additional agonist of any of the histamine H1, H2, H3, or H4 receptors.

11. The method of claim 1, wherein the first time interval is 2 to 4 days.

12. The method of claim 1, wherein the second time interval is 5 to 8 days.

13. The method of claim 2, wherein the third time interval is 12 to 16 days.

14. The method of claim 1, wherein the first and second doses comprise a subcutaneous injection of 0.01 to 0.1 mL histamine receptor activator composition.

15. The method of claim 14, wherein the first and second doses comprise a subcutaneous injection of 0.01 to 0.05 mL histamine receptor activator composition.

16. The method of claim 14, wherein the first and second doses comprise a subcutaneous injection of 0.05 mL histamine receptor activator composition.

17. The method of claim 1, wherein the first dose of histamine receptor activator composition is configured to activate a histamine H3 receptor and a histamine H4 receptor.

18. The method of claim 1, wherein the second dose of histamine receptor activator composition is configured to activate a histamine H1 receptor and a histamine H2 receptor.

* * * * *